United States Patent [19]

Hesse et al.

[11] Patent Number: 5,866,790
[45] Date of Patent: Feb. 2, 1999

[54] DNA SEQUENCES AND PLASMIDS FOR THE PREPARATION OF SUGAR BEET WITH CHANGED SUCROSE CONCENTRATION

[75] Inventors: Holger Hesse; Bernd Müller-Röber, both of Berlin, Germany

[73] Assignee: Hoechst Schering AgrEvo GmbH, Berlin, Germany

[21] Appl. No.: 553,436

[22] PCT Filed: May 20, 1994

[86] PCT No.: PCT/EP94/01671

§ 371 Date: Nov. 17, 1995

§ 102(e) Date: Nov. 17, 1995

[87] PCT Pub. No.: WO94/28146

PCT Pub. Date: Dec. 8, 1994

[30] Foreign Application Priority Data

May 24, 1993 [DE] Germany .......................... 43 17 596.1

[51] Int. Cl.⁶ .............................. A01H 5/00; C12N 15/00; C12N 15/29; C12N 5/04
[52] U.S. Cl. ........................ 800/205; 536/23.2; 536/23.6; 435/172.3; 435/419
[58] Field of Search ................................. 536/23.6, 23.2; 435/320.1, 419, 172.3, 91.1; 800/205

[56] References Cited

FOREIGN PATENT DOCUMENTS

| | | |
|---|---|---|
| 0438904 | 7/1991 | European Pat. Off. . |
| 0466995 | 1/1992 | European Pat. Off. . |
| 0530978 | 3/1992 | European Pat. Off. . |
| 9119806 | 12/1991 | WIPO . |
| 9216631 | 10/1992 | WIPO . |
| 9309237 | 5/1993 | WIPO . |

OTHER PUBLICATIONS

EMBL Sequence Database, Acc. No. S54379, Sucrose phosphate synthase release 35, Mar. 31, 1993.

M. Salanoubat, et al., "Molecular Cloning and Sequencing of Sucrose Synthase cDNA from Potato (*Solanum tuberosum* L.): Preliminary Characterization of Sucrose Synthase mRNA Distribution", Gene, vol. 60, 1987, pp. 47–56.

V.D. Sakalo, et al., "Characterization of Molecular Forms of Sucrose Synthase from Beet Roots", Biological Abstracts, vol. 95, Philadelphia, PA., Abstract No. 79002.

S. Fieuw, et al., "Sucrose Synthase and Sucrose Phosphate Synthase in Sugar Beet Plants Beta–Vulgaris –ssp–Altissima", Biological Abstracts, vol. 85, Philadelphia, PA., Abstract No. 72586.

Arai, M. et al. Plant Cell Physiol. vol. 33(4), pp. 503–506, 1992.

Napoli, C. et al. The Plant Cell, vol. 2, pp. 279–289, 1990.

Smith, C.J.S. et al. Nature, vol. 334, pp. 724–726, 1988.

Nagata, M. et al. Acta Horticulturae, No. 394, pp. 213–128 (abstract only cited), 1995.

*Primary Examiner*—Mary E. Mosher
*Attorney, Agent, or Firm*—Frommer Lawrence & Haug LLP

[57] ABSTRACT

DNA sequences and plasmids are described, that by integration in a plant genome of sugar beet change the sucrose concentration. In addition, transgenic plants that, by introduction of the DNA sequences of the invention, have altered sugar concentrations, are described.

35 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1925 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Beta vulgaris
        ( C ) INDIVIDUAL ISOLATE: ADP Glucose Pyrophosphorylase, large subunit ( v i i ) IMMEDIATE SOURCE:
        ( A ) LIBRARY: phage lamda zap ( i x ) FEATURE:
        ( A ) NAME/KEY: CDS
        ( B ) LOCATION: 206..1774

( x i ) SEQUENCE DESCRIPTION: SEQ ID NO:1:

```
CAAAAGAAAA  ACTTCCCATT  TCTACTTCTT  TGCACAATAT  AATTTCCCAC  CAATTTTTCT                60

TTAAATTTCT  CACTTTCATT  TAATCAGTTT  TCAGCAACAT  TCTGATACTC  GACAACCCAC               120

TTTCTGTTCT  CCCAAGATTC  CAAACCTCTG  ATTCTCATTC  CACTAATATT  TTTGCTTATT               180

TTTTTTCTGG  ATTTAAAGAA  AAGCT ATG GAT GCA AGT GCA GCA GCC ATA AAT                    232
                             Met Asp Ala Ser Ala Ala Ala Ile Asn
                              1                5

GTC AAT GCC CAT TTA ACA GAA GTT GGA AAG AAA CGT TTT TTA GGA GAG                      280
Val Asn Ala His Leu Thr Glu Val Gly Lys Lys Arg Phe Leu Gly Glu
 10              15                  20                      25

AGA ATC AGT CAA AGT TTG AAG GGT AAA GAT CTG AGA GCT CTG TTT TCA                      328
Arg Ile Ser Gln Ser Leu Lys Gly Lys Asp Leu Arg Ala Leu Phe Ser
                 30                  35                      40

AGA ACT GAG AGC AAG GGT AGA AAT GTC AAT AAA CCT GGG GTT GCA TTT                      376
Arg Thr Glu Ser Lys Gly Arg Asn Val Asn Lys Pro Gly Val Ala Phe
                 45                  50                      55
```

| | | | | | | | | | | | | | | | | |
|---|---|---|---|---|---|---|---|---|---|---|---|---|---|---|---|---|
| TCT | GTT | CTC | ACC | TCA | GAT | TTT | AAT | CAA | AGT | GTT | AAA | GAA | TCT | TTG | AAA | 424 |
| Ser | Val | Leu | Thr | Ser | Asp | Phe | Asn | Gln | Ser | Val | Lys | Glu | Ser | Leu | Lys | |
| | | 60 | | | | 65 | | | | | | 70 | | | | |
| TAT | GAG | CCA | GCA | TTA | TTT | GAA | TCT | CCA | AAA | GCT | GAC | CCA | AAA | AAT | GTG | 472 |
| Tyr | Glu | Pro | Ala | Leu | Phe | Glu | Ser | Pro | Lys | Ala | Asp | Pro | Lys | Asn | Val | |
| | 75 | | | | | 80 | | | | | 85 | | | | | |
| GCT | GCA | ATT | GTG | CTG | GGT | GGT | GGT | GCT | GGG | ACT | CGC | CTC | TTT | CCT | CTT | 520 |
| Ala | Ala | Ile | Val | Leu | Gly | Gly | Gly | Ala | Gly | Thr | Arg | Leu | Phe | Pro | Leu | |
| 90 | | | | | 95 | | | | | 100 | | | | | 105 | |
| ACT | AGC | AGG | AGA | GCT | AAG | CCA | GCA | GTG | CCA | ATT | GGA | GGG | TGT | TAC | AGG | 568 |
| Thr | Ser | Arg | Arg | Ala | Lys | Pro | Ala | Val | Pro | Ile | Gly | Gly | Cys | Tyr | Arg | |
| | | | | 110 | | | | | 115 | | | | | 120 | | |
| CTG | ATT | GAT | GTG | CCT | ATG | AGC | AAC | TGC | ATC | AAC | AGT | GGC | ATT | AGA | AAG | 616 |
| Leu | Ile | Asp | Val | Pro | Met | Ser | Asn | Cys | Ile | Asn | Ser | Gly | Ile | Arg | Lys | |
| | | | 125 | | | | | 130 | | | | | 135 | | | |
| ATT | TTC | ATT | CTT | ACC | CAG | TTC | AAT | TCG | TTT | TCG | CTT | AAT | CGT | CAT | CTT | 664 |
| Ile | Phe | Ile | Leu | Thr | Gln | Phe | Asn | Ser | Phe | Ser | Leu | Asn | Arg | His | Leu | |
| | | 140 | | | | | 145 | | | | | 150 | | | | |
| GCT | CGA | ACC | TAT | AAT | TTT | GGA | GAT | GGT | GTG | AAT | TTT | GGG | GAT | GGC | TTT | 712 |
| Ala | Arg | Thr | Tyr | Asn | Phe | Gly | Asp | Gly | Val | Asn | Phe | Gly | Asp | Gly | Phe | |
| | 155 | | | | | 160 | | | | | 165 | | | | | |
| GTG | GAG | GTT | TTT | GCT | GCT | ACA | CAA | ACA | CCT | GGA | GAA | TCA | GGA | AAG | AAA | 760 |
| Val | Glu | Val | Phe | Ala | Ala | Thr | Gln | Thr | Pro | Gly | Glu | Ser | Gly | Lys | Lys | |
| 170 | | | | | 175 | | | | | 180 | | | | | 185 | |
| TGG | TTC | CAG | GGC | ACC | GCT | GAT | GCA | GTA | AGA | CAG | TTT | TTC | TGG | GCA | TTT | 808 |
| Trp | Phe | Gln | Gly | Thr | Ala | Asp | Ala | Val | Arg | Gln | Phe | Phe | Trp | Ala | Phe | |
| | | | | 190 | | | | | 195 | | | | | 200 | | |
| GAG | GAT | TCC | AAA | TCC | AAG | GAT | GTC | GAG | CAT | ATA | GTT | ATT | TTA | TCC | GGT | 856 |
| Glu | Asp | Ser | Lys | Ser | Lys | Asp | Val | Glu | His | Ile | Val | Ile | Leu | Ser | Gly | |
| | | | 205 | | | | | 210 | | | | | 215 | | | |
| GAT | CAT | CTT | TAC | CGA | ATG | GAT | TAC | ATG | AGT | TTT | TGG | CAG | AAG | CAC | ATT | 904 |
| Asp | His | Leu | Tyr | Arg | Met | Asp | Tyr | Met | Ser | Phe | Trp | Gln | Lys | His | Ile | |
| | | 220 | | | | | 225 | | | | | 230 | | | | |
| GAC | ACC | AAT | GCT | GAT | ATT | ACA | GTG | TCA | TGC | ATA | CCC | ATG | GAT | GAC | AGC | 952 |
| Asp | Thr | Asn | Ala | Asp | Ile | Thr | Val | Ser | Cys | Ile | Pro | Met | Asp | Asp | Ser | |
| | | 235 | | | | | 240 | | | | | 245 | | | | |
| CGT | GCA | TCG | GAT | TAT | GGG | CTG | ATG | AAG | ATT | GAT | CAC | ACT | GGA | CGC | ATT | 1000 |
| Arg | Ala | Ser | Asp | Tyr | Gly | Leu | Met | Lys | Ile | Asp | His | Thr | Gly | Arg | Ile | |
| 250 | | | | | 255 | | | | | 260 | | | | | 265 | |
| GTC | CAT | TTT | GCA | GAA | AAA | CCC | AAG | GGT | TCT | GAT | CTA | ACA | GCA | ATG | CAA | 1048 |
| Val | His | Phe | Ala | Glu | Lys | Pro | Lys | Gly | Ser | Asp | Leu | Thr | Ala | Met | Gln | |
| | | | | 270 | | | | | 275 | | | | | 280 | | |
| GTA | GAT | ACA | ACT | GTT | CTT | GGG | CTC | TCT | GAC | CTT | GAA | GCT | ATG | TCA | AAT | 1096 |
| Val | Asp | Thr | Thr | Val | Leu | Gly | Leu | Ser | Asp | Leu | Glu | Ala | Met | Ser | Asn | |
| | | | 285 | | | | | 290 | | | | | 295 | | | |
| CCA | TAT | ATT | GCA | TCA | ATG | GGT | GTT | TAT | GTC | TTT | CGA | ACG | GAT | GTT | CTT | 1144 |
| Pro | Tyr | Ile | Ala | Ser | Met | Gly | Val | Tyr | Val | Phe | Arg | Thr | Asp | Val | Leu | |
| | | 300 | | | | | 305 | | | | | 310 | | | | |
| ATG | GAG | CTT | CTC | AAT | CGA | AAA | TAC | CCT | TCA | AGC | AAT | GAT | TTT | GGC | TCT | 1192 |
| Met | Glu | Leu | Leu | Asn | Arg | Lys | Tyr | Pro | Ser | Ser | Asn | Asp | Phe | Gly | Ser | |
| | 315 | | | | | 320 | | | | | 325 | | | | | |
| GAG | ATT | ATT | CCT | TCA | GCT | GTA | GGA | GAG | TCT | AAT | GTT | CAG | GCA | TAT | CTA | 1240 |
| Glu | Ile | Ile | Pro | Ser | Ala | Val | Gly | Glu | Ser | Asn | Val | Gln | Ala | Tyr | Leu | |
| 330 | | | | | 335 | | | | | 340 | | | | | 345 | |
| TTT | AAT | GAC | TAC | TGG | GAG | GAT | ATC | GGA | ACC | ATA | AAG | TCT | TTC | TTT | GAT | 1288 |
| Phe | Asn | Asp | Tyr | Trp | Glu | Asp | Ile | Gly | Thr | Ile | Lys | Ser | Phe | Phe | Asp | |
| | | | | 350 | | | | | 355 | | | | | 360 | | |
| TCC | AAT | TTG | GCC | CTT | ACA | CAA | CAG | CCT | CCC | AAG | TTT | GAA | TTC | TAC | GAT | 1336 |
| Ser | Asn | Leu | Ala | Leu | Thr | Gln | Gln | Pro | Pro | Lys | Phe | Glu | Phe | Tyr | Asp | |
| | | | | 365 | | | | | 370 | | | | | 375 | | |

| | | | | | | | | | | | | | | | | |
|---|---|---|---|---|---|---|---|---|---|---|---|---|---|---|---|---|
| CCA | AAA | ACA | CCT | TTT | TAT | ACA | TCT | GCA | AGA | TTT | CTG | CCT | CCT | ACA | AAA | 1384 |
| Pro | Lys | Thr | Pro | Phe | Tyr | Thr | Ser | Ala | Arg | Phe | Leu | Pro | Pro | Thr | Lys | |
| | | 380 | | | | | 385 | | | | | 390 | | | | |
| GTC | GAC | AGG | TGC | AAG | ATT | GTC | GAT | TCC | ATT | GTA | TCC | CAT | GGT | TGT | TTT | 1432 |
| Val | Asp | Arg | Cys | Lys | Ile | Val | Asp | Ser | Ile | Val | Ser | His | Gly | Cys | Phe | |
| 395 | | | | | | 400 | | | | | 405 | | | | | |
| CTA | CAG | GAG | TCT | AGC | ATC | CAA | CAT | TCC | ATT | GTT | GGT | GTT | CGC | TCA | AGA | 1480 |
| Leu | Gln | Glu | Ser | Ser | Ile | Gln | His | Ser | Ile | Val | Gly | Val | Arg | Ser | Arg | |
| 410 | | | | | 415 | | | | | 420 | | | | | 425 | |
| TTA | GAG | TCC | GGG | GTT | GAG | TTC | CAG | GAC | ACC | ATG | ATG | ATG | GGC | GCA | GAT | 1528 |
| Leu | Glu | Ser | Gly | Val | Glu | Phe | Gln | Asp | Thr | Met | Met | Met | Gly | Ala | Asp | |
| | | | | 430 | | | | | 435 | | | | | 440 | | |
| TAC | TAT | CAA | ACT | GAA | TCA | GAA | ATT | GCT | TCT | CTG | CTT | GCT | GAG | GGA | AAG | 1576 |
| Tyr | Tyr | Gln | Thr | Glu | Ser | Glu | Ile | Ala | Ser | Leu | Leu | Ala | Glu | Gly | Lys | |
| | | | 445 | | | | | 450 | | | | | 455 | | | |
| GTT | CCT | GTT | GGT | GTC | GGA | CAG | AAT | ACC | AAA | ATA | AAG | AAT | TGC | ATA | ATT | 1624 |
| Val | Pro | Val | Gly | Val | Gly | Gln | Asn | Thr | Lys | Ile | Lys | Asn | Cys | Ile | Ile | |
| | | 460 | | | | | 465 | | | | | 470 | | | | |
| GAC | AAG | AAC | GCC | AAA | ATT | GGA | AAA | GAT | GTG | GTA | ATC | GCA | AAC | ACG | GAT | 1672 |
| Asp | Lys | Asn | Ala | Lys | Ile | Gly | Lys | Asp | Val | Val | Ile | Ala | Asn | Thr | Asp | |
| | 475 | | | | | 480 | | | | | 485 | | | | | |
| GGT | GTT | GAG | GAA | GCA | GAT | AGA | CCA | AAT | GAA | GGC | TTT | TAC | ATC | AGG | TCG | 1720 |
| Gly | Val | Glu | Glu | Ala | Asp | Arg | Pro | Asn | Glu | Gly | Phe | Tyr | Ile | Arg | Ser | |
| 490 | | | | | 495 | | | | | 500 | | | | | 505 | |
| GGC | ATT | ACC | ATC | ATT | TTG | AAG | AAC | GCA | ACC | ATA | CAA | GAC | GGT | CTT | GTG | 1768 |
| Gly | Ile | Thr | Ile | Ile | Leu | Lys | Asn | Ala | Thr | Ile | Gln | Asp | Gly | Leu | Val | |
| | | | | 510 | | | | | 515 | | | | | 520 | | |
| ATT | TAG | ATTAATCAT | AACCTCATTA | GAAAGAAATA | ATTTTGCATG | ATTTCCTTTT | | | | | | | | | | 1824 |
| Ile | * | | | | | | | | | | | | | | | |

CATGTAACCT AAACTGGCTA AACCACGAGG TTTTCTCATC TGTATATATA ATATGTCTAT     1884

AACTATGGAT AATCTTAATA AAAAAAAAAA AAAAAAAAA A                          1925

( 2 ) INFORMATION FOR SEQ ID NO:2:

( i ) SEQUENCE CHARACTERISTICS:
        ( A ) LENGTH: 522 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Asp | Ala | Ser | Ala | Ala | Ala | Ile | Asn | Val | Asn | Ala | His | Leu | Thr | Glu |
| 1 | | | | 5 | | | | | 10 | | | | | 15 | |
| Val | Gly | Lys | Lys | Arg | Phe | Leu | Gly | Glu | Arg | Ile | Ser | Gln | Ser | Leu | Lys |
| | | | 20 | | | | | 25 | | | | | 30 | | |
| Gly | Lys | Asp | Leu | Arg | Ala | Leu | Phe | Ser | Arg | Thr | Glu | Ser | Lys | Gly | Arg |
| | | | 35 | | | | 40 | | | | | 45 | | | |
| Asn | Val | Asn | Lys | Pro | Gly | Val | Ala | Phe | Ser | Val | Leu | Thr | Ser | Asp | Phe |
| | | 50 | | | | | 55 | | | | | 60 | | | |
| Asn | Gln | Ser | Val | Lys | Glu | Ser | Leu | Lys | Tyr | Glu | Pro | Ala | Leu | Phe | Glu |
| 65 | | | | | 70 | | | | | 75 | | | | | 80 |
| Ser | Pro | Lys | Ala | Asp | Pro | Lys | Asn | Val | Ala | Ala | Ile | Val | Leu | Gly | Gly |
| | | | | 85 | | | | | 90 | | | | | 95 | |
| Gly | Ala | Gly | Thr | Arg | Leu | Phe | Pro | Leu | Thr | Ser | Arg | Arg | Ala | Lys | Pro |
| | | | 100 | | | | | 105 | | | | | 110 | | |
| Ala | Val | Pro | Ile | Gly | Gly | Cys | Tyr | Arg | Leu | Ile | Asp | Val | Pro | Met | Ser |
| | | 115 | | | | | 120 | | | | | 125 | | | |
| Asn | Cys | Ile | Asn | Ser | Gly | Ile | Arg | Lys | Ile | Phe | Ile | Leu | Thr | Gln | Phe |

|     |     |     |     |     | 130 |     |     |     |     | 135 |     |     |     |     | 140 |
| --- | --- | --- | --- | --- | --- | --- | --- | --- | --- | --- | --- | --- | --- | --- | --- |
| Asn<br>145 | Ser | Phe | Ser | Leu | Asn<br>150 | Arg | His | Leu | Ala | Arg<br>155 | Thr | Tyr | Asn | Phe | Gly<br>160 |
| Asp | Gly | Val | Asn | Phe<br>165 | Gly | Asp | Gly | Phe | Val<br>170 | Glu | Val | Phe | Ala | Ala<br>175 | Thr |
| Gln | Thr | Pro | Gly<br>180 | Glu | Ser | Gly | Lys | Lys<br>185 | Trp | Phe | Gln | Gly | Thr<br>190 | Ala | Asp |
| Ala | Val | Arg<br>195 | Gln | Phe | Phe | Trp | Ala<br>200 | Phe | Glu | Asp | Ser | Lys<br>205 | Ser | Lys | Asp |
| Val | Glu<br>210 | His | Ile | Val | Ile | Leu<br>215 | Ser | Gly | Asp | His | Leu<br>220 | Tyr | Arg | Met | Asp |
| Tyr<br>225 | Met | Ser | Phe | Trp | Gln<br>230 | Lys | His | Ile | Asp | Thr<br>235 | Asn | Ala | Asp | Ile | Thr<br>240 |
| Val | Ser | Cys | Ile | Pro<br>245 | Met | Asp | Asp | Ser | Arg<br>250 | Ala | Ser | Asp | Tyr | Gly<br>255 | Leu |
| Met | Lys | Ile | Asp<br>260 | His | Thr | Gly | Arg | Ile<br>265 | Val | His | Phe | Ala | Glu<br>270 | Lys | Pro |
| Lys | Gly | Ser<br>275 | Asp | Leu | Thr | Ala | Met<br>280 | Gln | Val | Asp | Thr | Thr<br>285 | Val | Leu | Gly |
| Leu | Ser<br>290 | Asp | Leu | Glu | Ala | Met<br>295 | Ser | Asn | Pro | Tyr | Ile<br>300 | Ala | Ser | Met | Gly |
| Val<br>305 | Tyr | Val | Phe | Arg | Thr<br>310 | Asp | Val | Leu | Met | Glu<br>315 | Leu | Leu | Asn | Arg | Lys<br>320 |
| Tyr | Pro | Ser | Ser | Asn<br>325 | Asp | Phe | Gly | Ser | Glu<br>330 | Ile | Ile | Pro | Ser | Ala<br>335 | Val |
| Gly | Glu | Ser | Asn<br>340 | Val | Gln | Ala | Tyr | Leu<br>345 | Phe | Asn | Asp | Tyr | Trp<br>350 | Glu | Asp |
| Ile | Gly | Thr<br>355 | Ile | Lys | Ser | Phe | Phe<br>360 | Asp | Ser | Asn | Leu | Ala<br>365 | Leu | Thr | Gln |
| Gln | Pro<br>370 | Pro | Lys | Phe | Glu | Phe<br>375 | Tyr | Asp | Pro | Lys | Thr<br>380 | Pro | Phe | Tyr | Thr |
| Ser<br>385 | Ala | Arg | Phe | Leu | Pro<br>390 | Pro | Thr | Lys | Val | Asp<br>395 | Arg | Cys | Lys | Ile | Val<br>400 |
| Asp | Ser | Ile | Val | Ser<br>405 | His | Gly | Cys | Phe | Leu<br>410 | Gln | Glu | Ser | Ser | Ile<br>415 | Gln |
| His | Ser | Ile | Val<br>420 | Gly | Val | Arg | Ser | Arg<br>425 | Leu | Glu | Ser | Gly | Val<br>430 | Glu | Phe |
| Gln | Asp | Thr<br>435 | Met | Met | Met | Gly | Ala<br>440 | Asp | Tyr | Tyr | Gln | Thr<br>445 | Glu | Ser | Glu |
| Ile | Ala<br>450 | Ser | Leu | Leu | Ala | Glu<br>455 | Gly | Lys | Val | Pro | Val<br>460 | Gly | Val | Gly | Gln |
| Asn<br>465 | Thr | Lys | Ile | Lys | Asn<br>470 | Cys | Ile | Ile | Asp | Lys<br>475 | Asn | Ala | Lys | Ile | Gly<br>480 |
| Lys | Asp | Val | Val | Ile<br>485 | Ala | Asn | Thr | Asp | Gly<br>490 | Val | Glu | Glu | Ala | Asp<br>495 | Arg |
| Pro | Asn | Glu | Gly<br>500 | Phe | Tyr | Ile | Arg | Ser<br>505 | Gly | Ile | Thr | Ile | Ile<br>510 | Leu | Lys |
| Asn | Ala | Thr<br>515 | Ile | Gln | Asp | Gly | Leu<br>520 | Val | Ile | | | | | | |

( 2 ) INFORMATION FOR SEQ ID NO:3:

( i ) SEQUENCE CHARACTERISTICS:
        ( A ) LENGTH: 1763 base pairs
        ( B ) TYPE: nucleic acid ( C ) STRANDEDNESS: single
( D ) TOPOLOGY: linear ( i i ) MOLECULE TYPE: cDNA ( v i ) ORIGINAL SOURCE:
( A ) ORGANISM: Beta vulgaris
( C ) INDIVIDUAL ISOLATE: ADP Glucose Pyrophosphorylase, small subunit ( v i i ) IMMEDIATE SOURCE:
( A ) LIBRARY: phage lamda zap ( i x ) FEATURE:
( A ) NAME/KEY: CDS
( B ) LOCATION: 3..1472

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| GG | ATA | ACT | GTG | CCA | TCA | ACC | TCC | TCA | AAG | AAC | CTC | CAA | AAT | AGC | CTC | 47 |
| | Ile | Thr | Val | Pro | Ser | Thr | Ser | Ser | Lys | Asn | Leu | Gln | Asn | Ser | Leu | |
| | 1 | | | | 5 | | | | | 10 | | | | | 15 | |
| GCA | TTC | TCC | TCT | TCT | TCT | CTC | TCC | GGC | GAC | AAA | ATT | CAA | ACG | ACG | TCA | 95 |
| Ala | Phe | Ser | Ser | Ser | Ser | Leu | Ser | Gly | Asp | Lys | Ile | Gln | Thr | Thr | Ser | |
| | | | | 20 | | | | | 25 | | | | | 30 | | |
| TTT | CTC | AAC | CGC | CGA | TAT | TGT | AGA | ATC | TCT | TCT | AGA | GCT | CCG | ATT | GTT | 143 |
| Phe | Leu | Asn | Arg | Arg | Tyr | Cys | Arg | Ile | Ser | Ser | Arg | Ala | Pro | Ile | Val | |
| | | | 35 | | | | | 40 | | | | | 45 | | | |
| GTC | TCT | CCC | AAA | GCT | GTT | TCT | GAT | TCT | AAG | AAT | TCG | CAG | ACT | TGT | CTT | 191 |
| Val | Ser | Pro | Lys | Ala | Val | Ser | Asp | Ser | Lys | Asn | Ser | Gln | Thr | Cys | Leu | |
| | | 50 | | | | | 55 | | | | | 60 | | | | |
| GAC | CCT | GAA | GCC | AGC | CGT | AGT | GTT | CTT | GGT | ATT | ATA | CTT | GGA | GGT | GGT | 239 |
| Asp | Pro | Glu | Ala | Ser | Arg | Ser | Val | Leu | Gly | Ile | Ile | Leu | Gly | Gly | Gly | |
| | | 65 | | | | | 70 | | | | | 75 | | | | |
| GCT | GGT | ACA | CGT | CTT | TAC | CCG | TTG | ACT | AAG | AAG | AGA | GCC | AAA | CCA | GCC | 287 |
| Ala | Gly | Thr | Arg | Leu | Tyr | Pro | Leu | Thr | Lys | Lys | Arg | Ala | Lys | Pro | Ala | |
| 80 | | | | | 85 | | | | | 90 | | | | | 95 | |
| GTG | CCA | CTC | GGT | GCT | AAT | TAT | AGG | CTT | ATT | GAT | ATC | CCA | GTG | AGC | AAT | 335 |
| Val | Pro | Leu | Gly | Ala | Asn | Tyr | Arg | Leu | Ile | Asp | Ile | Pro | Val | Ser | Asn | |
| | | | | 100 | | | | | 105 | | | | | 110 | | |
| TGT | TTG | AAC | AGT | AAT | ATT | TCC | AAA | ATA | TAT | GTT | CTT | ACA | CAA | TTC | AAT | 383 |
| Cys | Leu | Asn | Ser | Asn | Ile | Ser | Lys | Ile | Tyr | Val | Leu | Thr | Gln | Phe | Asn | |
| | | | 115 | | | | | 120 | | | | | 125 | | | |
| TCT | GCT | TCT | CTG | AAT | CGT | CAT | CTT | TCG | CGG | GCA | TAT | GCT | AGC | AAC | ATG | 431 |
| Ser | Ala | Ser | Leu | Asn | Arg | His | Leu | Ser | Arg | Ala | Tyr | Ala | Ser | Asn | Met | |
| | | 130 | | | | | 135 | | | | | 140 | | | | |
| GGA | GGA | TAC | AAA | AAT | GAG | GGG | TTT | GTA | GAA | GTT | CTT | GCT | GCT | CAG | CAA | 479 |
| Gly | Gly | Tyr | Lys | Asn | Glu | Gly | Phe | Val | Glu | Val | Leu | Ala | Ala | Gln | Gln | |
| | | 145 | | | | | 150 | | | | | 155 | | | | |
| AGT | CCA | GAG | AAT | CCA | AAC | TGG | TTT | CAG | GGT | ACA | GCT | GAT | GCT | GTT | AGG | 527 |
| Ser | Pro | Glu | Asn | Pro | Asn | Trp | Phe | Gln | Gly | Thr | Ala | Asp | Ala | Val | Arg | |
| 160 | | | | | 165 | | | | | 170 | | | | | 175 | |
| CAA | TAT | CTG | TGG | CTT | TTC | GAA | GAG | CAC | AAT | GTT | CTT | GAG | TAC | TTG | ATT | 575 |
| Gln | Tyr | Leu | Trp | Leu | Phe | Glu | Glu | His | Asn | Val | Leu | Glu | Tyr | Leu | Ile | |
| | | | | 180 | | | | | 185 | | | | | 190 | | |
| CTT | GCT | GGT | GAC | CAT | TTG | TAT | CGA | ATG | GAT | TAT | GAA | AGA | TTT | GTC | CAA | 623 |
| Leu | Ala | Gly | Asp | His | Leu | Tyr | Arg | Met | Asp | Tyr | Glu | Arg | Phe | Val | Gln | |
| | | | | 195 | | | | | 200 | | | | | 205 | | |
| GCT | CAC | AGA | GAA | ACT | GAT | GCA | GAC | ATT | ACT | GTT | GCT | GCA | TTG | CCA | ATG | 671 |
| Ala | His | Arg | Glu | Thr | Asp | Ala | Asp | Ile | Thr | Val | Ala | Ala | Leu | Pro | Met | |
| | | 210 | | | | | 215 | | | | | 220 | | | | |
| GAT | GAA | AAG | CGT | GCT | ACT | GCA | TTT | GGT | TTG | ATG | AAA | ATT | GAT | GAA | GAA | 719 |
| Asp | Glu | Lys | Arg | Ala | Thr | Ala | Phe | Gly | Leu | Met | Lys | Ile | Asp | Glu | Glu | |
| | | 225 | | | | | 230 | | | | | 235 | | | | |
| GGA | AGA | ATT | ATT | GAG | TTT | GCC | GAG | AAA | CCG | AAA | GGA | GAA | CAA | TTG | AAA | 767 |

```
Gly Arg Ile Ile Glu Phe Ala Glu Lys Pro Lys Gly Glu Gln Leu Lys
240                 245                 250                 255

GCT ATG AAG GTT GAT ACC ACA ATC CTG GGT CTG GAC GAT GAG AGA GCA      815
Ala Met Lys Val Asp Thr Thr Ile Leu Gly Leu Asp Asp Glu Arg Ala
                    260                 265                 270

AAA GAA ATG CCA TTC ATA GCC AGC ATG GGC ATA TAT GTT ATT AGC AAA      863
Lys Glu Met Pro Phe Ile Ala Ser Met Gly Ile Tyr Val Ile Ser Lys
                275                 280                 285

GAT GTA ATG CTT AAT CTG CTT CGG GAG CAA TTT CCT GGT GCT AAT GAT      911
Asp Val Met Leu Asn Leu Leu Arg Glu Gln Phe Pro Gly Ala Asn Asp
            290                 295                 300

TTT GGA AGT GAA GTT ATT CCA GGC GCC ACT TCC ATA GGG TTG AGA GTC      959
Phe Gly Ser Glu Val Ile Pro Gly Ala Thr Ser Ile Gly Leu Arg Val
    305                 310                 315

CAA GCT TAT TTG TAT GAT GGT TAC TGG GAG GAT ATT GGT ACC ATT GAA     1007
Gln Ala Tyr Leu Tyr Asp Gly Tyr Trp Glu Asp Ile Gly Thr Ile Glu
320                 325                 330                 335

GCT TTT TAC AAT GCT AAC TTG GGA ATC ACC AAA AAG CCG GTG CCA GAT     1055
Ala Phe Tyr Asn Ala Asn Leu Gly Ile Thr Lys Lys Pro Val Pro Asp
                340                 345                 350

TTT AGC TTC TAT GAT CGT TCA TCT CCA ATT TAT ACA CAA CCT CGG TAT     1103
Phe Ser Phe Tyr Asp Arg Ser Ser Pro Ile Tyr Thr Gln Pro Arg Tyr
            355                 360                 365

TTG CCT CCT TCA AAG ATG CTT GAT GCT GAT ATA ACT GAC AGC GTC ATC     1151
Leu Pro Pro Ser Lys Met Leu Asp Ala Asp Ile Thr Asp Ser Val Ile
    370                 375                 380

GGT GAA GGC TGT GTT ATT AAG AAC TGT AAG ATT CAT CAT TCT GTT ATC     1199
Gly Glu Gly Cys Val Ile Lys Asn Cys Lys Ile His His Ser Val Ile
385                 390                 395

GGA CTT CGA TCT TGT ATC TCG GAG GGT GCA ATC ATT GAG GAC ACA CTG     1247
Gly Leu Arg Ser Cys Ile Ser Glu Gly Ala Ile Ile Glu Asp Thr Leu
400                 405                 410                 415

TTG ATG GGA GCT GAT TAT TAT GAG ACT GAT GCT GAT CGG AAA TTC CTG     1295
Leu Met Gly Ala Asp Tyr Tyr Glu Thr Asp Ala Asp Arg Lys Phe Leu
                420                 425                 430

GCT GCT AAG GGT AGT GTA CCT ATT GGA ATT GGG AAT GCA CGT ATT GGG     1343
Ala Ala Lys Gly Ser Val Pro Ile Gly Ile Gly Asn Ala Arg Ile Gly
            435                 440                 445

GAT GAT GTC AAG ATT ATC AAC AGT GAC AAT GTA CAA GAA GCA GCA AGA     1391
Asp Asp Val Lys Ile Ile Asn Ser Asp Asn Val Gln Glu Ala Ala Arg
        450                 455                 460

GAA ACA GAC GGA TAC TTC ATA AAG AGC GGA ATA GTC ACT ATA ATC AAG     1439
Glu Thr Asp Gly Tyr Phe Ile Lys Ser Gly Ile Val Thr Ile Ile Lys
    465                 470                 475

GAC GCC ATG ATT CCA AGT GGA ACT GTA ATC TAG AAATGGAGCA TATAATAAAT   1492
Asp Ala Met Ile Pro Ser Gly Thr Val Ile *
480                 485                 490

ATCACTGCCT ATTTACAGTA CCTATCTGAG TCTCCCACCA TGACCCTTTG ATTCAATCTT   1552

TTAGTTATGT AAATATTTTT GGCTTTTGCG ATTTTGCCAT AAATTTGAAG AAGCGAGGAT   1612

TCAGGGACGA TAGTGCTATG AATTGGAAGA AAGGATTTGG GGGATATCTT TGTAAAGACA   1672

TTTTGACTAC TGGGCACTAA AAATTTGGTA ATGCTATACC AAAATATATA AAAAGATCTT   1732

GCTGGGTTTT GGTAAAAAAA AAAAAAAAAA A                                 1763
```

( 2 ) INFORMATION FOR SEQ ID NO:4:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ile | Thr | Val | Pro | Ser | Thr | Ser | Ser | Lys | Asn | Leu | Gln | Asn | Ser | Leu | Ala |
|---|---|---|---|---|---|---|---|---|---|---|---|---|---|---|---|
| 1 | | | | 5 | | | | | 10 | | | | | 15 | |

| Phe | Ser | Ser | Ser | Ser | Leu | Ser | Gly | Asp | Lys | Ile | Gln | Thr | Thr | Ser | Phe |
|---|---|---|---|---|---|---|---|---|---|---|---|---|---|---|---|
| | | | 20 | | | | | 25 | | | | | 30 | | |

| Leu | Asn | Arg | Arg | Tyr | Cys | Arg | Ile | Ser | Ser | Arg | Ala | Pro | Ile | Val | Val |
|---|---|---|---|---|---|---|---|---|---|---|---|---|---|---|---|
| | | 35 | | | | | 40 | | | | | 45 | | | |

| Ser | Pro | Lys | Ala | Val | Ser | Asp | Ser | Lys | Asn | Ser | Gln | Thr | Cys | Leu | Asp |
|---|---|---|---|---|---|---|---|---|---|---|---|---|---|---|---|
| | 50 | | | | | 55 | | | | | 60 | | | | |

| Pro | Glu | Ala | Ser | Arg | Ser | Val | Leu | Gly | Ile | Ile | Leu | Gly | Gly | Gly | Ala |
|---|---|---|---|---|---|---|---|---|---|---|---|---|---|---|---|
| 65 | | | | | 70 | | | | | 75 | | | | | 80 |

| Gly | Thr | Arg | Leu | Tyr | Pro | Leu | Thr | Lys | Lys | Arg | Ala | Lys | Pro | Ala | Val |
|---|---|---|---|---|---|---|---|---|---|---|---|---|---|---|---|
| | | | | 85 | | | | | 90 | | | | | 95 | |

| Pro | Leu | Gly | Ala | Asn | Tyr | Arg | Leu | Ile | Asp | Ile | Pro | Val | Ser | Asn | Cys |
|---|---|---|---|---|---|---|---|---|---|---|---|---|---|---|---|
| | | | 100 | | | | | 105 | | | | | 110 | | |

| Leu | Asn | Ser | Asn | Ile | Ser | Lys | Ile | Tyr | Val | Leu | Thr | Gln | Phe | Asn | Ser |
|---|---|---|---|---|---|---|---|---|---|---|---|---|---|---|---|
| | | 115 | | | | | 120 | | | | | 125 | | | |

| Ala | Ser | Leu | Asn | Arg | His | Leu | Ser | Arg | Ala | Tyr | Ala | Ser | Asn | Met | Gly |
|---|---|---|---|---|---|---|---|---|---|---|---|---|---|---|---|
| | 130 | | | | | 135 | | | | | 140 | | | | |

| Gly | Tyr | Lys | Asn | Glu | Gly | Phe | Val | Glu | Val | Leu | Ala | Ala | Gln | Gln | Ser |
|---|---|---|---|---|---|---|---|---|---|---|---|---|---|---|---|
| 145 | | | | | 150 | | | | | 155 | | | | | 160 |

| Pro | Glu | Asn | Pro | Asn | Trp | Phe | Gln | Gly | Thr | Ala | Asp | Ala | Val | Arg | Gln |
|---|---|---|---|---|---|---|---|---|---|---|---|---|---|---|---|
| | | | | 165 | | | | | 170 | | | | | 175 | |

| Tyr | Leu | Trp | Leu | Phe | Glu | Glu | His | Asn | Val | Leu | Glu | Tyr | Leu | Ile | Leu |
|---|---|---|---|---|---|---|---|---|---|---|---|---|---|---|---|
| | | | 180 | | | | | 185 | | | | | 190 | | |

| Ala | Gly | Asp | His | Leu | Tyr | Arg | Met | Asp | Tyr | Glu | Arg | Phe | Val | Gln | Ala |
|---|---|---|---|---|---|---|---|---|---|---|---|---|---|---|---|
| | | | 195 | | | | | 200 | | | | | 205 | | |

| His | Arg | Glu | Thr | Asp | Ala | Asp | Ile | Thr | Val | Ala | Ala | Leu | Pro | Met | Asp |
|---|---|---|---|---|---|---|---|---|---|---|---|---|---|---|---|
| | 210 | | | | | 215 | | | | | 220 | | | | |

| Glu | Lys | Arg | Ala | Thr | Ala | Phe | Gly | Leu | Met | Lys | Ile | Asp | Glu | Glu | Gly |
|---|---|---|---|---|---|---|---|---|---|---|---|---|---|---|---|
| 225 | | | | | 230 | | | | | 235 | | | | | 240 |

| Arg | Ile | Ile | Glu | Phe | Ala | Glu | Lys | Pro | Lys | Gly | Glu | Gln | Leu | Lys | Ala |
|---|---|---|---|---|---|---|---|---|---|---|---|---|---|---|---|
| | | | | 245 | | | | | 250 | | | | | 255 | |

| Met | Lys | Val | Asp | Thr | Thr | Ile | Leu | Gly | Leu | Asp | Asp | Glu | Arg | Ala | Lys |
|---|---|---|---|---|---|---|---|---|---|---|---|---|---|---|---|
| | | | 260 | | | | | 265 | | | | | 270 | | |

| Glu | Met | Pro | Phe | Ile | Ala | Ser | Met | Gly | Ile | Tyr | Val | Ile | Ser | Lys | Asp |
|---|---|---|---|---|---|---|---|---|---|---|---|---|---|---|---|
| | | 275 | | | | | 280 | | | | | 285 | | | |

| Val | Met | Leu | Asn | Leu | Leu | Arg | Glu | Gln | Phe | Pro | Gly | Ala | Asn | Asp | Phe |
|---|---|---|---|---|---|---|---|---|---|---|---|---|---|---|---|
| | 290 | | | | | 295 | | | | | 300 | | | | |

| Gly | Ser | Glu | Val | Ile | Pro | Gly | Ala | Thr | Ser | Ile | Gly | Leu | Arg | Val | Gln |
|---|---|---|---|---|---|---|---|---|---|---|---|---|---|---|---|
| 305 | | | | | 310 | | | | | 315 | | | | | 320 |

| Ala | Tyr | Leu | Tyr | Asp | Gly | Tyr | Trp | Glu | Asp | Ile | Gly | Thr | Ile | Glu | Ala |
|---|---|---|---|---|---|---|---|---|---|---|---|---|---|---|---|
| | | | | 325 | | | | | 330 | | | | | 335 | |

| Phe | Tyr | Asn | Ala | Asn | Leu | Gly | Ile | Thr | Lys | Lys | Pro | Val | Pro | Asp | Phe |
|---|---|---|---|---|---|---|---|---|---|---|---|---|---|---|---|
| | | | 340 | | | | | 345 | | | | | 350 | | |

| Ser | Phe | Tyr | Asp | Arg | Ser | Ser | Pro | Ile | Tyr | Thr | Gln | Pro | Arg | Tyr | Leu |
|---|---|---|---|---|---|---|---|---|---|---|---|---|---|---|---|
| | | 355 | | | | | 360 | | | | | 365 | | | |

| Pro | Pro | Ser | Lys | Met | Leu | Asp | Ala | Asp | Ile | Thr | Asp | Ser | Val | Ile | Gly |
|---|---|---|---|---|---|---|---|---|---|---|---|---|---|---|---|
| | 370 | | | | | 375 | | | | | 380 | | | | |

| Glu | Gly | Cys | Val | Ile | Lys | Asn | Cys | Lys | Ile | His | His | Ser | Val | Ile | Gly |
|---|---|---|---|---|---|---|---|---|---|---|---|---|---|---|---|
| 385 | | | | | 390 | | | | | 395 | | | | | 400 |

```
Leu  Arg  Ser  Cys  Ile  Ser  Glu  Gly  Ala  Ile  Ile  Glu  Asp  Thr  Leu  Leu
               405                      410                     415

Met  Gly  Ala  Asp  Tyr  Tyr  Glu  Thr  Asp  Ala  Asp  Arg  Lys  Phe  Leu  Ala
               420                      425                     430

Ala  Lys  Gly  Ser  Val  Pro  Ile  Gly  Ile  Gly  Asn  Ala  Arg  Ile  Gly  Asp
          435                      440                     445

Asp  Val  Lys  Ile  Ile  Asn  Ser  Asp  Asn  Val  Gln  Glu  Ala  Ala  Arg  Glu
     450                      455                     460

Thr  Asp  Gly  Tyr  Phe  Ile  Lys  Ser  Gly  Ile  Val  Thr  Ile  Ile  Lys  Asp
465                      470                     475                          480

Ala  Met  Ile  Pro  Ser  Gly  Thr  Val  Ile
                    485
```

(2) INFORMATION FOR SEQ ID NO:5:

(i) SEQUENCE CHARACTERISTICS:
        (A) LENGTH: 3635 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Beta vulgaris
        (C) INDIVIDUAL ISOLATE: Saccharosephosphate Synthase (vii) IMMEDIATE SOURCE:
        (A) LIBRARY: phage lamda zap (ix) FEATURE:
        (A) NAME/KEY: CDS
        (B) LOCATION: 30..3167

(xi) SEQUENCE DESCRIPTION: SEQ ID NO:5:

```
GGGCTGCAGG  GAAGCTCTGA  ACTTCAAAA  ATG  GCG  GGA  AAT  GAT  TGG  ATA  AAC        53
                                  Met  Ala  Gly  Asn  Asp  Trp  Ile  Asn
                                   1                    5

AGT  TAT  TTA  GAG  GCA  ATT  CTG  GAT  GTG  GGT  CCA  GGA  CTT  GAT  GAT  GCA  101
Ser  Tyr  Leu  Glu  Ala  Ile  Leu  Asp  Val  Gly  Pro  Gly  Leu  Asp  Asp  Ala
          10                      15                     20

AAA  TCA  TCT  TTG  CTT  TTG  AGA  GAA  AGA  GGC  AGG  TTT  AGT  CCT  ACT  CGT  149
Lys  Ser  Ser  Leu  Leu  Leu  Arg  Glu  Arg  Gly  Arg  Phe  Ser  Pro  Thr  Arg
25                       30                      35                           40

TAC  TTT  GTT  GAA  GAA  GTT  ATC  ACT  GGT  TTT  GAT  GAA  ACC  GAC  CTT  CAT  197
Tyr  Phe  Val  Glu  Glu  Val  Ile  Thr  Gly  Phe  Asp  Glu  Thr  Asp  Leu  His
               45                      50                      55

CGT  TCA  TGG  GTT  CGG  GCA  CAA  GCA  ACA  AGG  AGT  CCT  CAA  GAG  AGG  AAT  245
Arg  Ser  Trp  Val  Arg  Ala  Gln  Ala  Thr  Arg  Ser  Pro  Gln  Glu  Arg  Asn
               60                      65                      70

ACT  AGA  TTG  GAG  AAC  ATG  TGT  TGG  AGA  ATT  TGG  AAT  TTG  GCT  CGT  CAG  293
Thr  Arg  Leu  Glu  Asn  Met  Cys  Trp  Arg  Ile  Trp  Asn  Leu  Ala  Arg  Gln
               75                      80                      85

AAG  AAG  CAG  CTT  GAG  AAT  GAA  GAA  GCT  CAG  CGG  AAG  ACA  AAA  CGT  CGT  341
Lys  Lys  Gln  Leu  Glu  Asn  Glu  Glu  Ala  Gln  Arg  Lys  Thr  Lys  Arg  Arg
          90                       95                     100

ATG  GAG  CTT  GAG  AGG  GGT  CGT  CGA  GAA  GCA  ACT  GCT  GAT  ATG  TCG  GAG  389
Met  Glu  Leu  Glu  Arg  Gly  Arg  Arg  Glu  Ala  Thr  Ala  Asp  Met  Ser  Glu
105                      110                     115                         120

GAC  TTA  TCA  GAA  GGC  GAA  AAG  GAC  ATT  TCA  GCT  CAT  GGT  GAT  AGC  ACC  437
Asp  Leu  Ser  Glu  Gly  Glu  Lys  Asp  Ile  Ser  Ala  His  Gly  Asp  Ser  Thr
                    125                     130                     135

CGT  CCT  AGA  TTG  CCA  AGA  ATA  AAT  TCT  CTT  GAT  GCT  ATG  GAG  ACA  TGG  485
Arg  Pro  Arg  Leu  Pro  Arg  Ile  Asn  Ser  Leu  Asp  Ala  Met  Glu  Thr  Trp
```

```
                              140                           145                           150
ATT  AGT  CAA  CAA  AAG  GAA  AAA  AAA  CTC  TAC  CTT  GTT  TTG  ATA  AGT  CTT            533
Ile  Ser  Gln  Gln  Lys  Glu  Lys  Lys  Leu  Tyr  Leu  Val  Leu  Ile  Ser  Leu
          155                      160                      165

CAT  GGT  TTG  ATA  CGA  GGT  GAA  AAC  ATG  GAA  CTT  GGC  CGT  GAT  TCT  GAT            581
His  Gly  Leu  Ile  Arg  Gly  Glu  Asn  Met  Glu  Leu  Gly  Arg  Asp  Ser  Asp
          170                      175                      180

ACT  GGT  GGT  CAG  GTT  AAG  TAT  GTG  GTT  GAG  CTT  GCA  AGG  GCT  CTA  GGT            629
Thr  Gly  Gly  Gln  Val  Lys  Tyr  Val  Val  Glu  Leu  Ala  Arg  Ala  Leu  Gly
185                 190                      195                           200

TCG  ATG  CCA  GGT  GTT  TAT  AGA  GTT  GAT  TTG  CTA  ACT  AGG  CAA  GTT  TCA            677
Ser  Met  Pro  Gly  Val  Tyr  Arg  Val  Asp  Leu  Leu  Thr  Arg  Gln  Val  Ser
               205                           210                      215

TCT  CCT  GAC  GTG  GAT  TGG  AGT  TAT  GGG  GAG  CCT  ACT  GAG  ATG  CTG  AAT            725
Ser  Pro  Asp  Val  Asp  Trp  Ser  Tyr  Gly  Glu  Pro  Thr  Glu  Met  Leu  Asn
               220                      225                      230

CCA  AGG  GAT  TCC  AAT  GGT  TTT  GAT  GAT  GAT  GAT  GAT  GAA  ATG  GGA  GAG            773
Pro  Arg  Asp  Ser  Asn  Gly  Phe  Asp  Asp  Asp  Asp  Asp  Glu  Met  Gly  Glu
               235                      240                      245

AGT  AGT  GGT  GCT  TAC  ATT  GTT  CGT  ATA  CCA  TTT  GGG  CCG  AGG  GAT  AAG            821
Ser  Ser  Gly  Ala  Tyr  Ile  Val  Arg  Ile  Pro  Phe  Gly  Pro  Arg  Asp  Lys
          250                      255                      260

TAT  ATC  GCA  AAA  GAA  GAG  CTT  TGG  CCC  TAT  ATT  CCT  GAA  TTT  GTT  GAT            869
Tyr  Ile  Ala  Lys  Glu  Glu  Leu  Trp  Pro  Tyr  Ile  Pro  Glu  Phe  Val  Asp
265                      270                      275                      280

GGT  GCT  CTA  AAC  CAC  ATA  GTT  CAA  ATG  TCC  AAA  GTT  TTA  GGT  GAG  CAA            917
Gly  Ala  Leu  Asn  His  Ile  Val  Gln  Met  Ser  Lys  Val  Leu  Gly  Glu  Gln
                    285                      290                      295

ATT  GGT  AGC  GGG  GAA  ACA  GTT  TGG  CCA  GTT  GCC  ATT  CAT  GGA  CAT  TAT            965
Ile  Gly  Ser  Gly  Glu  Thr  Val  Trp  Pro  Val  Ala  Ile  His  Gly  His  Tyr
               300                      305                      310

GCT  GAT  GCT  GGT  GAT  TCT  GCT  GCT  CTT  CTT  TCT  GGT  GGC  CTA  AAT  GTT           1013
Ala  Asp  Ala  Gly  Asp  Ser  Ala  Ala  Leu  Leu  Ser  Gly  Gly  Leu  Asn  Val
               315                      320                      325

CCA  ATG  CTT  TTA  ACG  GGG  CAT  TCT  CTT  GGC  CGA  GAC  AAG  TTA  GAG  CAG           1061
Pro  Met  Leu  Leu  Thr  Gly  His  Ser  Leu  Gly  Arg  Asp  Lys  Leu  Glu  Gln
     330                      335                      340

CTC  CTC  AAA  CAG  GGT  CGA  ATG  TCT  AAA  GAT  GAC  ATA  AAC  AAT  ACA  TAC           1109
Leu  Leu  Lys  Gln  Gly  Arg  Met  Ser  Lys  Asp  Asp  Ile  Asn  Asn  Thr  Tyr
345                      350                      355                      360

AAA  ATA  ATG  CGT  AGG  ATA  GAA  GCC  GAA  GAG  TTA  TCA  CTT  GAT  GCC  TCT           1157
Lys  Ile  Met  Arg  Arg  Ile  Glu  Ala  Glu  Glu  Leu  Ser  Leu  Asp  Ala  Ser
                    365                      370                      375

GAG  ATA  GTC  ATA  ACT  AGT  ACA  AGA  CAA  GAA  ATA  GAA  GAG  CAA  TGG  CAC           1205
Glu  Ile  Val  Ile  Thr  Ser  Thr  Arg  Gln  Glu  Ile  Glu  Glu  Gln  Trp  His
               380                      385                      390

CTC  TAT  GAT  GGG  TTT  GAT  CCT  GTG  CTA  GAA  CGT  AAA  CTC  CGT  GCT  AGG           1253
Leu  Tyr  Asp  Gly  Phe  Asp  Pro  Val  Leu  Glu  Arg  Lys  Leu  Arg  Ala  Arg
          395                      400                      405

ATG  AAG  CGT  GGT  GTA  AGC  TGT  TAT  GGA  AGG  TTC  ATG  CCC  CGG  ATG  GTT           1301
Met  Lys  Arg  Gly  Val  Ser  Cys  Tyr  Gly  Arg  Phe  Met  Pro  Arg  Met  Val
     410                      415                      420

GTT  ATT  CCT  CCT  GGA  ATG  GAA  TTC  AAT  CAT  ATT  GTT  CCA  CAT  GAG  GGT           1349
Val  Ile  Pro  Pro  Gly  Met  Glu  Phe  Asn  His  Ile  Val  Pro  His  Glu  Gly
425                      430                      435                      440

GAT  ATG  GAT  GGT  GAA  ACA  GAA  GAA  ACT  GAA  GAG  CAT  CCT  ACA  TCA  CCT           1397
Asp  Met  Asp  Gly  Glu  Thr  Glu  Glu  Thr  Glu  Glu  His  Pro  Thr  Ser  Pro
                    445                      450                      455

GAT  CCA  CCT  ATC  TGG  GCT  GAG  ATT  ATG  CGC  TTC  TTT  TCT  AAA  CCA  AGG           1445
Asp  Pro  Pro  Ile  Trp  Ala  Glu  Ile  Met  Arg  Phe  Phe  Ser  Lys  Pro  Arg
```

-continued

|     |     |     |     |     | 460 |     |     |     | 465 |     |     |     |     | 470 |     |      |
|-----|-----|-----|-----|-----|-----|-----|-----|-----|-----|-----|-----|-----|-----|-----|-----|------|
| AAG | CCA | ATG | ATA | CTT | GCC | CTT | GCT | AGG | CCT | GAC | CCG | AAG | AAG | AAT | ATC | 1493 |
| Lys | Pro | Met | Ile | Leu | Ala | Leu | Ala | Arg | Pro | Asp | Pro | Lys | Lys | Asn | Ile |      |
|     |     | 475 |     |     |     |     | 480 |     |     |     |     | 485 |     |     |     |      |
| ACG | ACT | TTG | GTC | AAA | GCA | TTT | GGA | GAA | TGC | CGT | CCA | CTA | AGG | GAG | CTA | 1541 |
| Thr | Thr | Leu | Val | Lys | Ala | Phe | Gly | Glu | Cys | Arg | Pro | Leu | Arg | Glu | Leu |      |
|     | 490 |     |     |     |     | 495 |     |     |     |     | 500 |     |     |     |     |      |
| GCT | AAT | CTT | ACT | CTT | ATA | ATG | GGT | AAC | CGA | GAT | GGT | ATT | GAC | GAG | ATG | 1589 |
| Ala | Asn | Leu | Thr | Leu | Ile | Met | Gly | Asn | Arg | Asp | Gly | Ile | Asp | Glu | Met |      |
| 505 |     |     |     |     | 510 |     |     |     |     | 515 |     |     |     |     | 520 |      |
| TCA | AGC | ACC | AGT | TCT | TCA | GTT | CTC | CTG | TCA | GTG | CTT | AAG | CTA | ATT | GAT | 1637 |
| Ser | Ser | Thr | Ser | Ser | Ser | Val | Leu | Leu | Ser | Val | Leu | Lys | Leu | Ile | Asp |      |
|     |     |     |     | 525 |     |     |     |     | 530 |     |     |     |     | 535 |     |      |
| CAA | TAC | GAC | CTT | TAT | GGT | CAA | GTA | GCA | TAC | CCC | AAA | CAT | CAC | AAG | CAA | 1685 |
| Gln | Tyr | Asp | Leu | Tyr | Gly | Gln | Val | Ala | Tyr | Pro | Lys | His | His | Lys | Gln |      |
|     |     |     | 540 |     |     |     |     | 545 |     |     |     |     | 550 |     |     |      |
| GCT | GAT | GTT | CCT | GAG | ATT | TAT | CGT | TTG | GCA | GCA | AAG | ACA | AAG | GGA | GTC | 1733 |
| Ala | Asp | Val | Pro | Glu | Ile | Tyr | Arg | Leu | Ala | Ala | Lys | Thr | Lys | Gly | Val |      |
|     |     | 555 |     |     |     |     | 560 |     |     |     |     | 565 |     |     |     |      |
| TTT | ATT | AAT | CCA | GCT | TTT | ATT | GAG | CCA | TTT | GGG | CTG | ACT | CTA | ATA | GAG | 1781 |
| Phe | Ile | Asn | Pro | Ala | Phe | Ile | Glu | Pro | Phe | Gly | Leu | Thr | Leu | Ile | Glu |      |
| 570 |     |     |     |     | 575 |     |     |     |     | 580 |     |     |     |     |     |      |
| GCA | GCA | GCT | CAT | GGT | TTA | CCG | ATG | GTT | GCT | ACG | AAA | AAT | GGA | GGC | CCT | 1829 |
| Ala | Ala | Ala | His | Gly | Leu | Pro | Met | Val | Ala | Thr | Lys | Asn | Gly | Gly | Pro |      |
| 585 |     |     |     |     | 590 |     |     |     |     | 595 |     |     |     |     | 600 |      |
| GTT | GAT | ATC | CAG | AGG | GTC | CTT | GAT | AAT | GGT | CTT | CTT | GTG | GAT | CCT | CAT | 1877 |
| Val | Asp | Ile | Gln | Arg | Val | Leu | Asp | Asn | Gly | Leu | Leu | Val | Asp | Pro | His |      |
|     |     |     |     | 605 |     |     |     |     | 610 |     |     |     |     | 615 |     |      |
| GAG | CAG | CAG | TCT | ATT | GCT | ACT | GCT | TTG | CTG | AAG | CTT | GTT | GCT | GAT | AAG | 1925 |
| Glu | Gln | Gln | Ser | Ile | Ala | Thr | Ala | Leu | Leu | Lys | Leu | Val | Ala | Asp | Lys |      |
|     |     |     | 620 |     |     |     |     | 625 |     |     |     |     | 630 |     |     |      |
| CAA | CTA | TGG | ACA | AAA | TGC | CAG | CAA | AAT | GGA | CTG | AAA | AAT | ATT | CAT | CTC | 1973 |
| Gln | Leu | Trp | Thr | Lys | Cys | Gln | Gln | Asn | Gly | Leu | Lys | Asn | Ile | His | Leu |      |
|     |     | 635 |     |     |     |     | 640 |     |     |     |     | 645 |     |     |     |      |
| TAC | TCT | TGG | CCA | GAG | CAT | TCG | AAG | ACA | TAC | CTA | TCT | CGA | ATA | GCC | AGT | 2021 |
| Tyr | Ser | Trp | Pro | Glu | His | Ser | Lys | Thr | Tyr | Leu | Ser | Arg | Ile | Ala | Ser |      |
| 650 |     |     |     |     | 655 |     |     |     |     | 660 |     |     |     |     |     |      |
| TCG | AGA | CAA | AGG | CAA | CCA | CAG | TGG | CAA | AGA | AGT | AGT | GAT | GAA | GGG | CTT | 2069 |
| Ser | Arg | Gln | Arg | Gln | Pro | Gln | Trp | Gln | Arg | Ser | Ser | Asp | Glu | Gly | Leu |      |
| 665 |     |     |     |     | 670 |     |     |     |     | 675 |     |     |     |     | 680 |      |
| GAC | AAT | CAA | GAG | CCT | GAA | TCT | CCA | AGT | GAT | TCT | TTA | AGA | GAT | ATA | AAG | 2117 |
| Asp | Asn | Gln | Glu | Pro | Glu | Ser | Pro | Ser | Asp | Ser | Leu | Arg | Asp | Ile | Lys |      |
|     |     |     |     | 685 |     |     |     |     | 690 |     |     |     |     | 695 |     |      |
| GAT | ATA | TCT | CTA | AAC | CTT | GAA | GTT | CTC | GTT | AGA | CCG | GAG | AAA | AGG | GTG | 2165 |
| Asp | Ile | Ser | Leu | Asn | Leu | Glu | Val | Leu | Val | Arg | Pro | Glu | Lys | Arg | Val |      |
|     |     |     | 700 |     |     |     |     | 705 |     |     |     |     | 710 |     |     |      |
| AAG | ACG | TTG | AAA | ATC | TTG | GGA | TTG | ATG | ACA | AAA | GCA | AAT | TCG | AGA | ATG | 2213 |
| Lys | Thr | Leu | Lys | Ile | Leu | Gly | Leu | Met | Thr | Lys | Ala | Asn | Ser | Arg | Met |      |
|     |     | 715 |     |     |     |     | 720 |     |     |     |     | 725 |     |     |     |      |
| CTG | TTA | TGT | TCA | TGG | TCT | AAT | GGT | GTC | CAT | AAG | ATG | CTT | CGG | AAG | GCT | 2261 |
| Leu | Leu | Cys | Ser | Trp | Ser | Asn | Gly | Val | His | Lys | Met | Leu | Arg | Lys | Ala |      |
|     |     | 730 |     |     |     |     | 735 |     |     |     |     | 740 |     |     |     |      |
| CGG | TTC | TCT | GAC | AAA | GTA | GAT | CAG | GCT | TCT | AGT | AAA | TAT | CCA | GCA | TTT | 2309 |
| Arg | Phe | Ser | Asp | Lys | Val | Asp | Gln | Ala | Ser | Ser | Lys | Tyr | Pro | Ala | Phe |      |
| 745 |     |     |     |     | 750 |     |     |     |     | 755 |     |     |     |     | 760 |      |
| AGG | AGG | AGA | AAA | CTT | ATA | TAT | GTT | ATT | GCT | GTA | GAC | GGG | GAT | TAT | GAA | 2357 |
| Arg | Arg | Arg | Lys | Leu | Ile | Tyr | Val | Ile | Ala | Val | Asp | Gly | Asp | Tyr | Glu |      |
|     |     |     |     |     | 765 |     |     |     |     | 770 |     |     |     |     | 775 |      |
| GAT | GGA | CTT | TTT | GAT | ATT | GTT | CGG | AGG | ATA | TTT | GAT | GCT | GCT | GGC | AAG | 2405 |
| Asp | Gly | Leu | Phe | Asp | Ile | Val | Arg | Arg | Ile | Phe | Asp | Ala | Ala | Gly | Lys |      |

|  |  |  |  |  |  |  |  |  |  |  |  |  |  |  |  |  |
|---|---|---|---|---|---|---|---|---|---|---|---|---|---|---|---|---|
|  |  |  |  | 780 |  |  |  |  | 785 |  |  |  |  | 790 |  |  |
| GAG | AAG | ATT | GAA | GGT | TCC | ATC | GGG | TTT | ATA | TTG | TCA | ACA | TCC | TAT | TCT | 2453 |
| Glu | Lys | Ile | Glu | Gly | Ser | Ile | Gly | Phe | Ile | Leu | Ser | Thr | Ser | Tyr | Ser |  |
|  |  | 795 |  |  |  |  | 800 |  |  |  |  | 805 |  |  |  |  |
| ATG | CCC | GAA | ATT | CAG | AAC | TAT | TTG | CTA | TCA | AAA | GGC | TTC | AAT | CTT | CAT | 2501 |
| Met | Pro | Glu | Ile | Gln | Asn | Tyr | Leu | Leu | Ser | Lys | Gly | Phe | Asn | Leu | His |  |
|  | 810 |  |  |  |  | 815 |  |  |  |  | 820 |  |  |  |  |  |
| GAT | TTT | GAT | GCA | TAT | ATA | TGC | AAC | AGT | GGG | AGT | GAG | TTG | TAC | TAT | TCA | 2549 |
| Asp | Phe | Asp | Ala | Tyr | Ile | Cys | Asn | Ser | Gly | Ser | Glu | Leu | Tyr | Tyr | Ser |  |
| 825 |  |  |  |  | 830 |  |  |  |  | 835 |  |  |  |  | 840 |  |
| TCT | TTG | AAC | TCA | GAG | GAG | AGT | AAT | ATT | ATA | GCA | GAT | TCA | GAT | TAC | CAT | 2597 |
| Ser | Leu | Asn | Ser | Glu | Glu | Ser | Asn | Ile | Ile | Ala | Asp | Ser | Asp | Tyr | His |  |
|  |  |  |  | 845 |  |  |  |  | 850 |  |  |  |  | 855 |  |  |
| TCA | CAC | ATA | GAG | TAC | AGA | TGG | GGT | GGA | GAA | GGC | CTT | AGA | AGG | ACT | TTG | 2645 |
| Ser | His | Ile | Glu | Tyr | Arg | Trp | Gly | Gly | Glu | Gly | Leu | Arg | Arg | Thr | Leu |  |
|  |  | 860 |  |  |  |  | 865 |  |  |  |  | 870 |  |  |  |  |
| CTT | CGC | TGG | GCA | GCT | TCC | ATC | ACA | GAA | AAA | AAT | GGT | GAA | AAC | GAA | GAA | 2693 |
| Leu | Arg | Trp | Ala | Ala | Ser | Ile | Thr | Glu | Lys | Asn | Gly | Glu | Asn | Glu | Glu |  |
|  |  | 875 |  |  |  |  | 880 |  |  |  |  | 885 |  |  |  |  |
| CAG | GTT | ATT | ACT | GAA | GAT | GAA | GAA | GTT | TCT | ACG | GGT | TAT | TGC | TTT | GCG | 2741 |
| Gln | Val | Ile | Thr | Glu | Asp | Glu | Glu | Val | Ser | Thr | Gly | Tyr | Cys | Phe | Ala |  |
|  | 890 |  |  |  |  | 895 |  |  |  |  | 900 |  |  |  |  |  |
| TTT | AAA | ATA | AAG | AAC | CAA | AAT | AAG | GTT | CCC | CCT | ACG | AAG | GAG | CTC | CGC | 2789 |
| Phe | Lys | Ile | Lys | Asn | Gln | Asn | Lys | Val | Pro | Pro | Thr | Lys | Glu | Leu | Arg |  |
| 905 |  |  |  |  | 910 |  |  |  |  | 915 |  |  |  |  | 920 |  |
| AAG | TCA | ATG | AGG | ATT | CAA | GCT | CTT | CGT | TGC | CAT | GTG | ATT | TAC | TGT | CAG | 2837 |
| Lys | Ser | Met | Arg | Ile | Gln | Ala | Leu | Arg | Cys | His | Val | Ile | Tyr | Cys | Gln |  |
|  |  |  |  | 925 |  |  |  |  | 930 |  |  |  |  | 935 |  |  |
| AAC | GGA | TCT | AAA | ATG | AAT | GTG | ATT | CCA | GTA | CTA | GCA | TCC | CGT | TCT | CAA | 2885 |
| Asn | Gly | Ser | Lys | Met | Asn | Val | Ile | Pro | Val | Leu | Ala | Ser | Arg | Ser | Gln |  |
|  |  | 940 |  |  |  |  |  |  | 945 |  |  |  |  | 950 |  |  |
| GCC | CTC | AGG | TAT | CTT | TAT | GTT | CGT | TGG | GGA | GTT | GAG | TTG | TCG | AAG | ATG | 2933 |
| Ala | Leu | Arg | Tyr | Leu | Tyr | Val | Arg | Trp | Gly | Val | Glu | Leu | Ser | Lys | Met |  |
|  |  | 955 |  |  |  |  | 960 |  |  |  |  | 965 |  |  |  |  |
| GTT | GTC | TTT | GTT | GGA | GAA | TGT | GGT | GAC | ACA | GAT | TAT | GAA | GGC | TTG | CTT | 2981 |
| Val | Val | Phe | Val | Gly | Glu | Cys | Gly | Asp | Thr | Asp | Tyr | Glu | Gly | Leu | Leu |  |
|  | 970 |  |  |  |  | 975 |  |  |  |  | 980 |  |  |  |  |  |
| GGC | GGG | GTC | CAT | AAA | ACC | GTA | ATA | CTG | AAG | GGA | GTC | TCC | AAC | ACT | GCT | 3029 |
| Gly | Gly | Val | His | Lys | Thr | Val | Ile | Leu | Lys | Gly | Val | Ser | Asn | Thr | Ala |  |
| 985 |  |  |  | 990 |  |  |  |  | 995 |  |  |  |  |  | 1000 |  |
| TTA | AGG | TCT | CTC | CAT | GCC | AAC | AGA | AGT | TAC | CCT | CTT | TCA | CAT | GTC | GTG | 3077 |
| Leu | Arg | Ser | Leu | His | Ala | Asn | Arg | Ser | Tyr | Pro | Leu | Ser | His | Val | Val |  |
|  |  |  |  | 1005 |  |  |  |  | 1010 |  |  |  |  | 1015 |  |  |
| TCG | CTT | GAC | AGC | CCC | AAT | ATT | GGC | GAG | GTG | AGC | AAA | GGG | TGC | AGC | AGC | 3125 |
| Ser | Leu | Asp | Ser | Pro | Asn | Ile | Gly | Glu | Val | Ser | Lys | Gly | Cys | Ser | Ser |  |
|  |  |  | 1020 |  |  |  |  | 1025 |  |  |  |  | 1030 |  |  |  |
| TCC | GAG | ATC | CAG | TCC | ATC | GTC | ACA | AAA | CTC | TCC | AAA | GCT | TAA |  |  | 3167 |
| Ser | Glu | Ile | Gln | Ser | Ile | Val | Thr | Lys | Leu | Ser | Lys | Ala | * |  |  |  |
|  |  | 1035 |  |  |  |  | 1040 |  |  |  |  | 1045 |  |  |  |  |
| TCAGATATCT | GCTGCTTTCT | TTTGGGTAAG | CAAGGTTTCA | TCTTATATGA | TTATATCATA |  |  |  |  |  |  |  |  |  |  | 3227 |
| AGATACTATA | TAAGCACCTT | ATTGGTAAGT | CAGTCCCATA | ATAATAATGT | ACTTCAGAAC |  |  |  |  |  |  |  |  |  |  | 3287 |
| CACAATACTT | AAAAGTTGGT | TCAGTAGTGA | TTAGTCTCAT | AATAATCATA | TAATTACACA |  |  |  |  |  |  |  |  |  |  | 3347 |
| TCCGCTGTTA | ACTAGTGGTA | ATATCTAAGC | TCAACAATAA | AGATGTAAAA | TGCTAGTATG |  |  |  |  |  |  |  |  |  |  | 3407 |
| GAAATGAATT | GCTAGCTGTT | GATCTCTTTC | CCTTTATTCT | GTATTATTTC | TTTCCTCATC |  |  |  |  |  |  |  |  |  |  | 3467 |
| TCATGTAAAA | ACAATTTTCT | GAAGGTGTAC | AGTTTTTCC | CCTTATATAT | CTGTATTATT |  |  |  |  |  |  |  |  |  |  | 3527 |
| TCTACTATTT | TTTGTTTGTA | AGAATATCCT | CTCATCGAGG | AGTGATAATT | AAATAACCGG |  |  |  |  |  |  |  |  |  |  | 3587 |

CTTGCTAAAT ATAAAGCTTA TTCGAGTTAA AAAAAAAAAA AAAAAAA    3635

( 2 ) INFORMATION FOR SEQ ID NO:6:

( i ) SEQUENCE CHARACTERISTICS:
        ( A ) LENGTH: 1045 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Gly Asn Asp Trp Ile Asn Ser Tyr Leu Glu Ala Ile Leu Asp
  1               5                  10                  15

Val Gly Pro Gly Leu Asp Asp Ala Lys Ser Ser Leu Leu Leu Arg Glu
             20                  25                  30

Arg Gly Arg Phe Ser Pro Thr Arg Tyr Phe Val Glu Glu Val Ile Thr
         35                  40                  45

Gly Phe Asp Glu Thr Asp Leu His Arg Ser Trp Val Arg Ala Gln Ala
     50                  55                  60

Thr Arg Ser Pro Gln Glu Arg Asn Thr Arg Leu Glu Asn Met Cys Trp
 65                  70                  75                  80

Arg Ile Trp Asn Leu Ala Arg Gln Lys Lys Gln Leu Glu Asn Glu Glu
                 85                  90                  95

Ala Gln Arg Lys Thr Lys Arg Arg Met Glu Leu Glu Arg Gly Arg Arg
                100                 105                 110

Glu Ala Thr Ala Asp Met Ser Glu Asp Leu Ser Glu Gly Glu Lys Asp
            115                 120                 125

Ile Ser Ala His Gly Asp Ser Thr Arg Pro Arg Leu Pro Arg Ile Asn
130                 135                 140

Ser Leu Asp Ala Met Glu Thr Trp Ile Ser Gln Gln Lys Glu Lys Lys
145                 150                 155                 160

Leu Tyr Leu Val Leu Ile Ser Leu His Gly Leu Ile Arg Gly Glu Asn
                165                 170                 175

Met Glu Leu Gly Arg Asp Ser Asp Thr Gly Gly Gln Val Lys Tyr Val
            180                 185                 190

Val Glu Leu Ala Arg Ala Leu Gly Ser Met Pro Gly Val Tyr Arg Val
        195                 200                 205

Asp Leu Leu Thr Arg Gln Val Ser Ser Pro Asp Val Asp Trp Ser Tyr
210                 215                 220

Gly Glu Pro Thr Glu Met Leu Asn Pro Arg Asp Ser Asn Gly Phe Asp
225                 230                 235                 240

Asp Asp Asp Asp Glu Met Gly Glu Ser Ser Gly Ala Tyr Ile Val Arg
                245                 250                 255

Ile Pro Phe Gly Pro Arg Asp Lys Tyr Ile Ala Lys Glu Glu Leu Trp
            260                 265                 270

Pro Tyr Ile Pro Glu Phe Val Asp Gly Ala Leu Asn His Ile Val Gln
        275                 280                 285

Met Ser Lys Val Leu Gly Glu Gln Ile Gly Ser Gly Glu Thr Val Trp
        290                 295                 300

Pro Val Ala Ile His Gly His Tyr Ala Asp Ala Gly Asp Ser Ala Ala
305                 310                 315                 320

Leu Leu Ser Gly Gly Leu Asn Val Pro Met Leu Leu Thr Gly His Ser
                325                 330                 335

Leu Gly Arg Asp Lys Leu Glu Gln Leu Leu Lys Gln Gly Arg Met Ser
            340                 345                 350
```

```
Lys  Asp  Asp  Ile  Asn  Asn  Thr  Tyr  Lys  Ile  Met  Arg  Arg  Ile  Glu  Ala
          355                      360                     365

Glu  Glu  Leu  Ser  Leu  Asp  Ala  Ser  Glu  Ile  Val  Ile  Thr  Ser  Thr  Arg
370                      375                     380

Gln  Glu  Ile  Glu  Glu  Gln  Trp  His  Leu  Tyr  Asp  Gly  Phe  Asp  Pro  Val
385                      390                     395                      400

Leu  Glu  Arg  Lys  Leu  Arg  Ala  Arg  Met  Lys  Arg  Gly  Val  Ser  Cys  Tyr
               405                     410                      415

Gly  Arg  Phe  Met  Pro  Arg  Met  Val  Val  Ile  Pro  Pro  Gly  Met  Glu  Phe
               420                     425                      430

Asn  His  Ile  Val  Pro  His  Glu  Gly  Asp  Met  Asp  Gly  Glu  Thr  Glu  Glu
          435                     440                      445

Thr  Glu  Glu  His  Pro  Thr  Ser  Pro  Asp  Pro  Pro  Ile  Trp  Ala  Glu  Ile
450                      455                     460

Met  Arg  Phe  Phe  Ser  Lys  Pro  Arg  Lys  Pro  Met  Ile  Leu  Ala  Leu  Ala
465                      470                     475                      480

Arg  Pro  Asp  Pro  Lys  Lys  Asn  Ile  Thr  Thr  Leu  Val  Lys  Ala  Phe  Gly
               485                     490                      495

Glu  Cys  Arg  Pro  Leu  Arg  Glu  Leu  Ala  Asn  Leu  Thr  Leu  Ile  Met  Gly
               500                     505                      510

Asn  Arg  Asp  Gly  Ile  Asp  Glu  Met  Ser  Ser  Thr  Ser  Ser  Val  Leu
          515                     520                      525

Leu  Ser  Val  Leu  Lys  Leu  Ile  Asp  Gln  Tyr  Asp  Leu  Tyr  Gly  Gln  Val
530                      535                     540

Ala  Tyr  Pro  Lys  His  His  Lys  Gln  Ala  Asp  Val  Pro  Glu  Ile  Tyr  Arg
545                      550                     555                      560

Leu  Ala  Ala  Lys  Thr  Lys  Gly  Val  Phe  Ile  Asn  Pro  Ala  Phe  Ile  Glu
               565                     570                      575

Pro  Phe  Gly  Leu  Thr  Leu  Ile  Glu  Ala  Ala  His  Gly  Leu  Pro  Met
               580                     585                      590

Val  Ala  Thr  Lys  Asn  Gly  Gly  Pro  Val  Asp  Ile  Gln  Arg  Val  Leu  Asp
               595                     600                      605

Asn  Gly  Leu  Leu  Val  Asp  Pro  His  Glu  Gln  Gln  Ser  Ile  Ala  Thr  Ala
     610                     615                      620

Leu  Leu  Lys  Leu  Val  Ala  Asp  Lys  Gln  Leu  Trp  Thr  Lys  Cys  Gln  Gln
625                      630                     635                      640

Asn  Gly  Leu  Lys  Asn  Ile  His  Leu  Tyr  Ser  Trp  Pro  Glu  His  Ser  Lys
               645                     650                      655

Thr  Tyr  Leu  Ser  Arg  Ile  Ala  Ser  Ser  Arg  Gln  Arg  Gln  Pro  Gln  Trp
               660                     665                      670

Gln  Arg  Ser  Ser  Asp  Glu  Gly  Leu  Asp  Asn  Gln  Glu  Pro  Glu  Ser  Pro
          675                     680                      685

Ser  Asp  Ser  Leu  Arg  Asp  Ile  Lys  Asp  Ile  Ser  Leu  Asn  Leu  Glu  Val
     690                     695                      700

Leu  Val  Arg  Pro  Glu  Lys  Arg  Val  Lys  Thr  Leu  Lys  Ile  Leu  Gly  Leu
705                      710                     715                      720

Met  Thr  Lys  Ala  Asn  Ser  Arg  Met  Leu  Leu  Cys  Ser  Trp  Ser  Asn  Gly
               725                     730                      735

Val  His  Lys  Met  Leu  Arg  Lys  Ala  Arg  Phe  Ser  Asp  Lys  Val  Asp  Gln
               740                     745                      750

Ala  Ser  Ser  Lys  Tyr  Pro  Ala  Phe  Arg  Arg  Arg  Lys  Leu  Ile  Tyr  Val
          755                     760                      765

Ile  Ala  Val  Asp  Gly  Asp  Tyr  Glu  Asp  Gly  Leu  Phe  Asp  Ile  Val  Arg
               770                     775                      780
```

| Arg | Ile | Phe | Asp | Ala | Ala | Gly | Lys | Glu | Lys | Ile | Glu | Gly | Ser | Ile | Gly |
| 785 | | | | | 790 | | | | 795 | | | | | | 800 |

| Phe | Ile | Leu | Ser | Thr | Ser | Tyr | Ser | Met | Pro | Glu | Ile | Gln | Asn | Tyr | Leu |
| | | | | 805 | | | | | 810 | | | | | 815 | |

| Leu | Ser | Lys | Gly | Phe | Asn | Leu | His | Asp | Phe | Asp | Ala | Tyr | Ile | Cys | Asn |
| | | | 820 | | | | | 825 | | | | | 830 | | |

| Ser | Gly | Ser | Glu | Leu | Tyr | Tyr | Ser | Ser | Leu | Asn | Ser | Glu | Ser | Asn |
| | | 835 | | | | | 840 | | | | | 845 | | |

| Ile | Ile | Ala | Asp | Ser | Asp | Tyr | His | Ser | His | Ile | Glu | Tyr | Arg | Trp | Gly |
| | | 850 | | | | | 855 | | | | | 860 | | | |

| Gly | Glu | Gly | Leu | Arg | Arg | Thr | Leu | Leu | Arg | Trp | Ala | Ala | Ser | Ile | Thr |
| 865 | | | | | 870 | | | | 875 | | | | | | 880 |

| Glu | Lys | Asn | Gly | Glu | Asn | Glu | Glu | Gln | Val | Ile | Thr | Glu | Asp | Glu | Glu |
| | | | | 885 | | | | | 890 | | | | | 895 | |

| Val | Ser | Thr | Gly | Tyr | Cys | Phe | Ala | Phe | Lys | Ile | Lys | Asn | Gln | Asn | Lys |
| | | | 900 | | | | | 905 | | | | | 910 | | |

| Val | Pro | Pro | Thr | Lys | Glu | Leu | Arg | Lys | Ser | Met | Arg | Ile | Gln | Ala | Leu |
| | | | 915 | | | | 920 | | | | | 925 | | | |

| Arg | Cys | His | Val | Ile | Tyr | Cys | Gln | Asn | Gly | Ser | Lys | Met | Asn | Val | Ile |
| | 930 | | | | | 935 | | | | | 940 | | | | |

| Pro | Val | Leu | Ala | Ser | Arg | Ser | Gln | Ala | Leu | Arg | Tyr | Leu | Tyr | Val | Arg |
| 945 | | | | | 950 | | | | | 955 | | | | | 960 |

| Trp | Gly | Val | Glu | Leu | Ser | Lys | Met | Val | Val | Phe | Val | Gly | Glu | Cys | Gly |
| | | | | 965 | | | | | 970 | | | | | 975 | |

| Asp | Thr | Asp | Tyr | Glu | Gly | Leu | Leu | Gly | Gly | Val | His | Lys | Thr | Val | Ile |
| | | | 980 | | | | | 985 | | | | | 990 | | |

| Leu | Lys | Gly | Val | Ser | Asn | Thr | Ala | Leu | Arg | Ser | Leu | His | Ala | Asn | Arg |
| | | 995 | | | | | 1000 | | | | | 1005 | | | |

| Ser | Tyr | Pro | Leu | Ser | His | Val | Val | Ser | Leu | Asp | Ser | Pro | Asn | Ile | Gly |
| | 1010 | | | | | 1015 | | | | | 1020 | | | | |

| Glu | Val | Ser | Lys | Gly | Cys | Ser | Ser | Ser | Glu | Ile | Gln | Ser | Ile | Val | Thr |
| 1025 | | | | | 1030 | | | | | 1035 | | | | | 1040 |

| Lys | Leu | Ser | Lys | Ala |
| | | | | 1045 |

( 2 ) INFORMATION FOR SEQ ID NO:7:

( i ) SEQUENCE CHARACTERISTICS:
    ( A ) LENGTH: 2563 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Beta vulgaris
    ( C ) INDIVIDUAL ISOLATE: Saccharosesynthase ( v i i ) IMMEDIATE SOURCE:
    ( A ) LIBRARY: phage lamda zap ( i x ) FEATURE:
    ( A ) NAME/KEY: CDS
    ( B ) LOCATION: 3..2303

( x i ) SEQUENCE DESCRIPTION: SEQ ID NO:7:

| CT | GCA | GGA | GGG | AAA | CAA | ATT | CTT | AGC | GAT | GGC | CCG | TTT | AGC | GAA | GTT | 47 |
| | Ala | Gly | Gly | Lys | Gln | Ile | Leu | Ser | Asp | Gly | Pro | Phe | Ser | Glu | Val | |
| | 1 | | | | 5 | | | | | 10 | | | | | 15 | |

| | | | | | | | | | | | | | | | | |
|---|---|---|---|---|---|---|---|---|---|---|---|---|---|---|---|---|
| CTT | AGG | TCT | GCT | CAG | GAA | GCA | ATA | GTT | GTT | CCT | CCC | TTT | GTT | GCT | ATA | 95 |
| Leu | Arg | Ser | Ala | Gln 20 | Glu | Ala | Ile | Val 25 | Val | Pro | Pro | Phe | Val | Ala 30 | Ile | |
| GCA | GTC | CGT | CCA | AGA | CCT | GGA | GTT | TGG | GAA | TAT | GTT | CGT | GTT | AAT | GTC | 143 |
| Ala | Val | Arg 35 | Pro | Arg | Pro | Gly | Val | Trp 40 | Glu | Tyr | Val | Arg | Val 45 | Asn | Val | |
| TCT | GAA | CTG | AAT | GTG | GAG | CAG | CTA | ACT | GTG | TCT | GAG | TAT | CTC | CAT | TTC | 191 |
| Ser | Glu | Leu | Asn 50 | Val | Glu | Gln | Leu | Thr 55 | Val | Ser | Glu | Tyr | Leu 60 | His | Phe | |
| AAG | GAA | GAA | CTT | GTG | GAT | GGA | AAG | GCT | GAT | GAC | CAC | TAT | GTG | CTT | GAG | 239 |
| Lys | Glu 65 | Glu | Leu | Val | Asp | Gly 70 | Lys | Ala | Asp | Asp | His 75 | Tyr | Val | Leu | Glu | |
| CTT | GAT | TTC | GAG | CCT | TTT | AAT | GAA | TCA | GTT | CCA | CGT | CCA | ACT | CGC | TCT | 287 |
| Leu 80 | Asp | Phe | Glu | Pro | Phe 85 | Asn | Glu | Ser | Val | Pro 90 | Arg | Pro | Thr | Arg | Ser 95 | |
| TCA | TCA | ATT | GGT | AAT | GGT | GTT | CAG | TTC | CTC | AAT | CGG | CAC | CTG | TCA | TCA | 335 |
| Ser | Ser | Ile | Gly | Asn 100 | Gly | Val | Gln | Phe | Leu 105 | Asn | Arg | His | Leu | Ser 110 | Ser | |
| AGC | ATG | TTC | TGC | AAC | AAA | GAT | TGC | TTG | GAG | CCG | TTA | CTT | GAT | TTT | CTT | 383 |
| Ser | Met | Phe | Cys 115 | Asn | Lys | Asp | Cys | Leu 120 | Glu | Pro | Leu | Leu | Asp 125 | Phe | Leu | |
| AGA | GTG | CAC | AAA | CAT | AAA | GGA | GTT | GTC | ATG | ATG | TTG | AAT | GAT | CGG | ATA | 431 |
| Arg | Val | His 130 | Lys | His | Lys | Gly | Val 135 | Val | Met | Met | Leu | Asn 140 | Asp | Arg | Ile | |
| CAG | ACT | ATC | CAG | CGT | CTT | CAG | TCT | GCA | TTG | TCT | AAA | GCT | GAG | GAT | TAT | 479 |
| Gln | Thr | Ile 145 | Gln | Arg | Leu | Gln | Ser 150 | Ala | Leu | Ser | Lys | Ala 155 | Glu | Asp | Tyr | |
| CTT | ATC | AAA | CTT | CCA | GCA | GAT | ACA | CCT | TAC | TCT | GAG | TTC | GAA | TTT | GTA | 527 |
| Leu 160 | Ile | Lys | Leu | Pro | Ala 165 | Asp | Thr | Pro | Tyr | Ser 170 | Glu | Phe | Glu | Phe | Val 175 | |
| ATC | CAA | GGT | ATG | GGT | TTT | GAA | AGA | GGC | TGG | GGT | GAT | ACT | GCT | GAA | AGG | 575 |
| Ile | Gln | Gly | Met | Gly 180 | Phe | Glu | Arg | Gly | Trp 185 | Gly | Asp | Thr | Ala | Glu 190 | Arg | |
| GTT | CTA | GAA | ATG | ATG | CAT | CTA | CTA | CTA | GAT | ATC | CTT | CAG | GCT | CCC | GAT | 623 |
| Val | Leu | Glu | Met 195 | Met | His | Leu | Leu | Leu 200 | Asp | Ile | Leu | Gln | Ala 205 | Pro | Asp | |
| CCG | TCT | ACA | TTA | GAG | ACA | TTT | CTG | GGA | AGA | CTT | CCC | ATG | GTG | TTT | AAT | 671 |
| Pro | Ser | Thr 210 | Leu | Glu | Thr | Phe | Leu 215 | Gly | Arg | Leu | Pro | Met 220 | Val | Phe | Asn | |
| GTG | GTC | ATT | TTG | TCT | GTA | CAT | GGA | TAT | TTT | GGA | CAG | GCA | CAT | GTG | CTC | 719 |
| Val | Val | Ile 225 | Leu | Ser | Val | His | Gly 230 | Tyr | Phe | Gly | Gln | Ala 235 | His | Val | Leu | |
| GGC | TTG | CCT | GAC | ACT | GGT | GGG | CAG | ATA | GTT | TAT | ATA | CTT | GAC | CAA | GTG | 767 |
| Gly | Leu | Pro | Asp 240 | Thr | Gly | Gly | Gln | Ile 245 | Val | Tyr | Ile | Leu | Asp 250 | Gln | Val 255 | |
| CGG | TCT | CTG | GAA | CAT | GAA | ATG | CTC | CAA | CGA | ATA | AAG | AAG | CAA | GGA | CTA | 815 |
| Arg | Ser | Leu | Glu | His 260 | Glu | Met | Leu | Gln | Arg 265 | Ile | Lys | Lys | Gln | Gly 270 | Leu | |
| GAT | GTG | ACT | CCT | AGA | ATT | CTT | ATC | GTG | AGT | CGG | TTG | ATT | CCT | GAC | GCT | 863 |
| Asp | Val | Thr | Pro 275 | Arg | Ile | Leu | Ile | Val 280 | Ser | Arg | Leu | Ile | Pro 285 | Asp | Ala | |
| AAA | GGG | ACC | ACG | TGC | AAT | CAA | CGT | ATG | GAG | AAA | GTC | AGT | GGA | ACA | GAG | 911 |
| Lys | Gly | Thr | Thr 290 | Cys | Asn | Gln | Arg | Met 295 | Glu | Lys | Val | Ser | Gly 300 | Thr | Glu | |
| CAT | GCT | AGT | ATC | CTG | AGA | GTT | CCT | TTC | CGA | TCA | GAG | AAA | GGA | ATC | CTC | 959 |
| His | Ala | Ser | Ile 305 | Leu | Arg | Val | Pro | Phe 310 | Arg | Ser | Glu | Lys | Gly 315 | Ile | Leu | |
| CGC | AAA | TGG | ATA | TCT | AGA | TTT | GAT | GTA | TGG | CCT | TAT | TTA | GAG | ACC | TTC | 1007 |
| Arg | Lys | Trp | Ile | Ser 320 | Arg | Phe | Asp | Val | Trp 325 | Pro | Tyr | Leu | Glu | Thr 330 | Phe 335 | |

| | | | | | | | | | | | | | | | | |
|---|---|---|---|---|---|---|---|---|---|---|---|---|---|---|---|---|
| ACT | GAG | GAT | GCA | GCT | GGT | GAA | ATT | ATT | GGC | GAG | TTG | CAG | GGT | CGT | CCA | 1055 |
| Thr | Glu | Asp | Ala | Ala | Gly | Glu | Ile | Ile | Gly | Glu | Leu | Gln | Gly | Arg | Pro | |
| | | | 340 | | | | | 345 | | | | | | 350 | | |
| GAT | CTG | ATA | ATT | GGC | AAC | TAC | AGC | GAT | GGG | AAT | ATA | GTT | GCT | TCT | TTA | 1103 |
| Asp | Leu | Ile | Ile | Gly | Asn | Tyr | Ser | Asp | Gly | Asn | Ile | Val | Ala | Ser | Leu | |
| | | | 355 | | | | | 360 | | | | | | 365 | | |
| TTG | TCC | CAC | AAA | ATG | GGT | GTC | ACC | CAG | TGC | AAT | ATA | GCC | CAT | GCA | TTG | 1151 |
| Leu | Ser | His | Lys | Met | Gly | Val | Thr | Gln | Cys | Asn | Ile | Ala | His | Ala | Leu | |
| | | 370 | | | | | 375 | | | | | | 380 | | | |
| GAG | AAA | ACC | AAG | TAT | CCA | GAT | TCT | GAT | ATT | TAC | TGG | AAA | AGA | TTT | GAG | 1199 |
| Glu | Lys | Thr | Lys | Tyr | Pro | Asp | Ser | Asp | Ile | Tyr | Trp | Lys | Arg | Phe | Glu | |
| 385 | | | | | 390 | | | | | 395 | | | | | | |
| GAC | AAA | TAT | CAC | TTC | TCG | TGT | CAA | TTT | TCA | GCT | GAC | TTG | ATG | GCA | ATG | 1247 |
| Asp | Lys | Tyr | His | Phe | Ser | Cys | Gln | Phe | Ser | Ala | Asp | Leu | Met | Ala | Met | |
| 400 | | | | | 405 | | | | | 410 | | | | | 415 | |
| AAT | CAT | GCT | GAT | TTC | ATC | ATT | ACG | AGT | ACT | TAC | CAA | GAG | ATA | GCT | GGA | 1295 |
| Asn | His | Ala | Asp | Phe | Ile | Ile | Thr | Ser | Thr | Tyr | Gln | Glu | Ile | Ala | Gly | |
| | | | | 420 | | | | | 425 | | | | | 430 | | |
| ACG | AAG | AAT | ACT | GTT | GGT | CAA | TAT | GAA | AGC | CAT | AAG | GCC | TTT | ACT | TTT | 1343 |
| Thr | Lys | Asn | Thr | Val | Gly | Gln | Tyr | Glu | Ser | His | Lys | Ala | Phe | Thr | Phe | |
| | | | 435 | | | | | 440 | | | | | 445 | | | |
| CCG | GGG | CTG | TAT | CGG | GTG | GTT | CAC | GGG | ATT | GAT | GTC | TTT | GAT | CCC | AAG | 1391 |
| Pro | Gly | Leu | Tyr | Arg | Val | Val | His | Gly | Ile | Asp | Val | Phe | Asp | Pro | Lys | |
| | | 450 | | | | | 455 | | | | | 460 | | | | |
| TTT | AAT | ATT | GTC | TCG | CCA | GGG | GCA | GAC | ATG | GCC | ATC | TAC | TTC | CCA | TTT | 1439 |
| Phe | Asn | Ile | Val | Ser | Pro | Gly | Ala | Asp | Met | Ala | Ile | Tyr | Phe | Pro | Phe | |
| 465 | | | | | 470 | | | | | 475 | | | | | | |
| TCA | GAG | AAG | GAT | GTC | ACC | TGT | CTC | ACT | TCA | CTT | CAT | AGA | CTT | ATA | GAG | 1487 |
| Ser | Glu | Lys | Asp | Val | Thr | Cys | Leu | Thr | Ser | Leu | His | Arg | Leu | Ile | Glu | |
| 480 | | | | | 485 | | | | | 490 | | | | | 495 | |
| CAG | CTC | CTA | TTC | AAA | CCT | GAG | CAG | AAC | GAA | GAA | CAC | ATT | GGT | GTA | TTA | 1535 |
| Gln | Leu | Leu | Phe | Lys | Pro | Glu | Gln | Asn | Glu | Glu | His | Ile | Gly | Val | Leu | |
| | | | | 500 | | | | | 505 | | | | | 510 | | |
| GAT | GAT | ACC | TCA | AAG | CCA | ATT | ATA | TTT | TCC | ATG | GCG | AGG | CTA | GAC | CGT | 1583 |
| Asp | Asp | Thr | Ser | Lys | Pro | Ile | Ile | Phe | Ser | Met | Ala | Arg | Leu | Asp | Arg | |
| | | | 515 | | | | | 520 | | | | | 525 | | | |
| GTG | AAG | AAT | ATA | ACA | GGG | CTG | GTA | GAG | TGC | TAT | GGC | AAG | AAT | GCG | AAA | 1631 |
| Val | Lys | Asn | Ile | Thr | Gly | Leu | Val | Glu | Cys | Tyr | Gly | Lys | Asn | Ala | Lys | |
| | | 530 | | | | | 535 | | | | | 540 | | | | |
| CTC | AGG | GAA | CTG | GCA | AAC | CTG | GTT | GTA | GTG | GCT | GGG | TAC | AAT | GAT | GTA | 1679 |
| Leu | Arg | Glu | Leu | Ala | Asn | Leu | Val | Val | Val | Ala | Gly | Tyr | Asn | Asp | Val | |
| 545 | | | | | 550 | | | | | 555 | | | | | | |
| AAA | AAG | TCG | AAT | GAC | AGG | GAG | GAA | ATT | GCC | GAA | ATC | GAG | AAG | ATG | CAC | 1727 |
| Lys | Lys | Ser | Asn | Asp | Arg | Glu | Glu | Ile | Ala | Glu | Ile | Glu | Lys | Met | His | |
| 560 | | | | | 565 | | | | | 570 | | | | | 575 | |
| AGG | CTT | ATA | CAG | GAG | TAT | AAT | TTA | AGA | GGA | CAA | TTT | CGC | TGG | ATT | GCT | 1775 |
| Arg | Leu | Ile | Gln | Glu | Tyr | Asn | Leu | Arg | Gly | Gln | Phe | Arg | Trp | Ile | Ala | |
| | | | | 580 | | | | | 585 | | | | | 590 | | |
| TCT | CAA | ACA | AAT | AGA | GTA | CGA | AAT | GGT | GAA | CTC | TAT | CGC | TAC | ATT | TGT | 1823 |
| Ser | Gln | Thr | Asn | Arg | Val | Arg | Asn | Gly | Glu | Leu | Tyr | Arg | Tyr | Ile | Cys | |
| | | | 595 | | | | | 600 | | | | | 605 | | | |
| GAC | AAA | GGA | GGT | ATT | TTT | GCG | CAG | CCT | GCA | TTT | TAT | GAA | GCA | TTT | GGG | 1871 |
| Asp | Lys | Gly | Gly | Ile | Phe | Ala | Gln | Pro | Ala | Phe | Tyr | Glu | Ala | Phe | Gly | |
| | | 610 | | | | | 615 | | | | | 620 | | | | |
| CTT | ACA | GTT | GTT | GAA | GCC | ATG | ACC | TGT | GGT | CTT | CCC | ACA | TTT | GCT | ACC | 1919 |
| Leu | Thr | Val | Val | Glu | Ala | Met | Thr | Cys | Gly | Leu | Pro | Thr | Phe | Ala | Thr | |
| 625 | | | | | 630 | | | | | 635 | | | | | | |
| TGC | CAC | GGT | GGT | CCA | GCT | GAG | ATT | ATA | GAA | GAC | GGT | GTT | TCA | GGA | TTT | 1967 |
| Cys | His | Gly | Gly | Pro | Ala | Glu | Ile | Ile | Glu | Asp | Gly | Val | Ser | Gly | Phe | |
| 640 | | | | | 645 | | | | | 650 | | | | | 655 | |

| | | | | | | | | | | | | | | | |
|---|---|---|---|---|---|---|---|---|---|---|---|---|---|---|---|
| CAT | ATC | GAT | CCA | TAT | CAT | GCT | GAT | CAG | GCA | GAA | AAA | ATG | ACT | GAA | TTC | 2015
| His | Ile | Asp | Pro | Tyr | His | Ala | Asp | Gln | Ala | Glu | Lys | Met | Thr | Glu | Phe |
| | | | 660 | | | | | 665 | | | | | 670 | | |
| TTT | GTC | AAG | TGC | AGA | GAG | GAT | CCA | AAC | TAC | TGG | ACT | AAA | ATC | TCT | GCA | 2063
| Phe | Val | Lys | Cys | Arg | Glu | Asp | Pro | Asn | Tyr | Trp | Thr | Lys | Ile | Ser | Ala |
| | | | 675 | | | | | 680 | | | | | 685 | | |
| GGA | GGG | TTA | CTA | AGG | ATC | AAA | GAA | AGA | TAT | ACC | TGG | CAA | AAG | TAT | TCT | 2111
| Gly | Gly | Leu | Leu | Arg | Ile | Lys | Glu | Arg | Tyr | Thr | Trp | Gln | Lys | Tyr | Ser |
| | | 690 | | | | | 695 | | | | | 700 | | | |
| GAA | AGG | TTA | ATG | ACA | TTG | GCA | GGG | GTG | TAT | GGT | TTC | TGG | AAA | TAT | GTC | 2159
| Glu | Arg | Leu | Met | Thr | Leu | Ala | Gly | Val | Tyr | Gly | Phe | Trp | Lys | Tyr | Val |
| | 705 | | | | | 710 | | | | | 715 | | | | |
| TCT | AAA | CTA | GAG | AGA | AGA | GAG | ACA | CGA | CGT | TAT | CTT | GAG | ATG | TTC | TAC | 2207
| Ser | Lys | Leu | Glu | Arg | Arg | Glu | Thr | Arg | Arg | Tyr | Leu | Glu | Met | Phe | Tyr |
| 720 | | | | | 725 | | | | | 730 | | | | | 735 |
| ATT | TTG | AAG | TTC | CGT | GAT | CTG | GCC | AAC | TCT | GTT | CCG | CTG | GCA | ACA | GAT | 2255
| Ile | Leu | Lys | Phe | Arg | Asp | Leu | Ala | Asn | Ser | Val | Pro | Leu | Ala | Thr | Asp |
| | | | | 740 | | | | | 745 | | | | | 750 | |
| GAA | GAG | CCT | TCT | ACT | ACT | GAT | GCA | GTT | GCG | ACA | TTC | CGT | GGA | CCT | TGA | 2303
| Glu | Glu | Pro | Ser | Thr | Thr | Asp | Ala | Val | Ala | Thr | Phe | Arg | Gly | Pro | * |
| | | | 755 | | | | | 760 | | | | | 765 | | |

| | | | | |
|---|---|---|---|---|
| ACGCTGCTGC | TTACTGAGGT | TCCAAGTTGT | GTATATATTA | CTGTGAAAGG | AATAAGTGTA | 2363
| GCTACACAAA | AGGTTCTCAA | CTATTAGTAT | CTTCTCTGTG | TAAATAACGA | GAGTGAAAAA | 2423
| TGTAATATTG | TTGATGTCTT | GAAAACTGAG | TTTGCTTTGT | TTATTTTAA | GTGTATGACA | 2483
| ATATGTATCA | TATAACGGAT | TCTTCAGTGA | TCATATCAAA | AACTACTGAC | CATCGAAGTT | 2543
| AATGAAAATC | GACAGCAACA | | | | | 2563

( 2 ) INFORMATION FOR SEQ ID NO:8:

( i ) SEQUENCE CHARACTERISTICS:
        ( A ) LENGTH: 766 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Ala | Gly | Gly | Lys | Gln | Ile | Leu | Ser | Asp | Gly | Pro | Phe | Ser | Glu | Val | Leu |
| 1 | | | | 5 | | | | | 10 | | | | | 15 | |
| Arg | Ser | Ala | Gln | Glu | Ala | Ile | Val | Val | Pro | Pro | Phe | Val | Ala | Ile | Ala |
| | | | 20 | | | | | 25 | | | | | 30 | | |
| Val | Arg | Pro | Arg | Pro | Gly | Val | Trp | Glu | Tyr | Val | Arg | Val | Asn | Val | Ser |
| | | 35 | | | | | 40 | | | | | 45 | | | |
| Glu | Leu | Asn | Val | Glu | Gln | Leu | Thr | Val | Ser | Glu | Tyr | Leu | His | Phe | Lys |
| | 50 | | | | | 55 | | | | | 60 | | | | |
| Glu | Glu | Leu | Val | Asp | Gly | Lys | Ala | Asp | Asp | His | Tyr | Val | Leu | Glu | Leu |
| 65 | | | | | 70 | | | | | 75 | | | | | 80 |
| Asp | Phe | Glu | Pro | Phe | Asn | Glu | Ser | Val | Pro | Arg | Pro | Thr | Arg | Ser | Ser |
| | | | | 85 | | | | | 90 | | | | | 95 | |
| Ser | Ile | Gly | Asn | Gly | Val | Gln | Phe | Leu | Asn | Arg | His | Leu | Ser | Ser | Ser |
| | | | 100 | | | | | 105 | | | | | 110 | | |
| Met | Phe | Cys | Asn | Lys | Asp | Cys | Leu | Glu | Pro | Leu | Leu | Asp | Phe | Leu | Arg |
| | | 115 | | | | | 120 | | | | | 125 | | | |
| Val | His | Lys | His | Lys | Gly | Val | Val | Met | Met | Leu | Asn | Asp | Arg | Ile | Gln |
| | 130 | | | | | 135 | | | | | 140 | | | | |
| Thr | Ile | Gln | Arg | Leu | Gln | Ser | Ala | Leu | Ser | Lys | Ala | Glu | Asp | Tyr | Leu |
| 145 | | | | | 150 | | | | | 155 | | | | | 160 |

| | | | | | | | | | | | | | | |
|---|---|---|---|---|---|---|---|---|---|---|---|---|---|---|
|Ile|Lys|Leu|Pro|Ala 165|Asp|Thr|Pro|Tyr|Ser 170|Glu|Phe|Glu|Phe 175|Val|Ile|
|Gln|Gly|Met|Gly 180|Phe|Glu|Arg|Gly 185|Trp|Gly|Asp|Thr|Ala 190|Glu|Arg|Val|
|Leu|Glu|Met 195|Met|His|Leu|Leu|Leu 200|Asp|Ile|Leu|Gln 205|Ala|Pro|Asp|Pro|
|Ser|Thr 210|Leu|Glu|Thr|Phe|Leu 215|Gly|Arg|Leu|Pro|Met 220|Val|Phe|Asn|Val|
|Val 225|Ile|Leu|Ser|Val|His 230|Gly|Tyr|Phe|Gly|Gln 235|Ala|His|Val|Leu|Gly 240|
|Leu|Pro|Asp|Thr|Gly 245|Gly|Gln|Ile|Val|Tyr 250|Ile|Leu|Asp|Gln|Val 255|Arg|
|Ser|Leu|Glu|His 260|Glu|Met|Leu|Gln|Arg 265|Ile|Lys|Lys|Gln|Gly 270|Leu|Asp|
|Val|Thr|Pro 275|Arg|Ile|Leu|Ile|Val 280|Ser|Arg|Leu|Ile|Pro 285|Asp|Ala|Lys|
|Gly|Thr 290|Thr|Cys|Asn|Gln|Arg 295|Met|Glu|Lys|Val|Ser 300|Gly|Thr|Glu|His|
|Ala 305|Ser|Ile|Leu|Arg|Val 310|Pro|Phe|Arg|Ser|Glu 315|Lys|Gly|Ile|Leu|Arg 320|
|Lys|Trp|Ile|Ser|Arg 325|Phe|Asp|Val|Trp|Pro 330|Tyr|Leu|Glu|Thr|Phe 335|Thr|
|Glu|Asp|Ala|Ala 340|Gly|Glu|Ile|Ile|Gly 345|Glu|Leu|Gln|Gly|Arg 350|Pro|Asp|
|Leu|Ile|Ile 355|Gly|Asn|Tyr|Ser|Asp 360|Gly|Asn|Ile|Val|Ala 365|Ser|Leu|Leu|
|Ser|His 370|Lys|Met|Gly|Val|Thr 375|Gln|Cys|Asn|Ile|Ala 380|His|Ala|Leu|Glu|
|Lys|Thr 385|Lys|Tyr|Pro|Asp 390|Ser|Asp|Ile|Tyr|Trp 395|Lys|Arg|Phe|Glu|Asp 400|
|Lys|Tyr|His|Phe|Ser 405|Cys|Gln|Phe|Ser|Ala 410|Asp|Leu|Met|Ala|Met 415|Asn|
|His|Ala|Asp|Phe 420|Ile|Ile|Thr|Ser|Thr 425|Tyr|Gln|Glu|Ile|Ala 430|Gly|Thr|
|Lys|Asn|Thr 435|Val|Gly|Gln|Tyr|Glu 440|Ser|His|Lys|Ala|Phe 445|Thr|Phe|Pro|
|Gly|Leu 450|Tyr|Arg|Val|Val|His 455|Gly|Ile|Asp|Val|Phe 460|Asp|Pro|Lys|Phe|
|Asn 465|Ile|Val|Ser|Pro|Gly 470|Ala|Asp|Met|Ala|Ile 475|Tyr|Phe|Pro|Phe|Ser 480|
|Glu|Lys|Asp|Val|Thr 485|Cys|Leu|Thr|Ser|Leu 490|His|Arg|Leu|Ile|Glu 495|Gln|
|Leu|Leu|Phe|Lys 500|Pro|Glu|Gln|Asn|Glu 505|Glu|His|Ile|Gly|Val 510|Leu|Asp|
|Asp|Thr|Ser 515|Lys|Pro|Ile|Ile|Phe 520|Ser|Met|Ala|Arg|Leu 525|Asp|Arg|Val|
|Lys|Asn 530|Ile|Thr|Gly|Leu|Val 535|Glu|Cys|Tyr|Gly|Lys 540|Asn|Ala|Lys|Leu|
|Arg 545|Glu|Leu|Ala|Asn|Leu 550|Val|Val|Val|Ala|Gly 555|Tyr|Asn|Asp|Val|Lys 560|
|Lys|Ser|Asn|Asp|Arg 565|Glu|Glu|Ile|Ala|Glu 570|Ile|Glu|Lys|Met|His 575|Arg|
|Leu|Ile|Gln|Glu|Tyr 580|Asn|Leu|Arg|Gly|Gln 585|Phe|Arg|Trp|Ile|Ala 590|Ser|

| Gln | Thr | Asn 595 | Arg | Val | Arg | Asn | Gly 600 | Glu | Leu | Tyr | Arg | Tyr 605 | Ile | Cys | Asp |
| Lys | Gly 610 | Gly | Ile | Phe | Ala | Gln 615 | Pro | Ala | Phe | Tyr | Glu 620 | Ala | Phe | Gly | Leu |
| Thr 625 | Val | Val | Glu | Ala | Met 630 | Thr | Cys | Gly | Leu | Pro 635 | Thr | Phe | Ala | Thr | Cys 640 |
| His | Gly | Gly | Pro | Ala 645 | Glu | Ile | Ile | Glu | Asp 650 | Gly | Val | Ser | Gly | Phe 655 | His |
| Ile | Asp | Pro | Tyr 660 | His | Ala | Asp | Gln | Ala 665 | Glu | Lys | Met | Thr | Glu 670 | Phe | Phe |
| Val | Lys | Cys 675 | Arg | Glu | Asp | Pro | Asn 680 | Tyr | Trp | Thr | Lys | Ile 685 | Ser | Ala | Gly |
| Gly | Leu 690 | Leu | Arg | Ile | Lys | Glu 695 | Arg | Tyr | Thr | Trp | Gln 700 | Lys | Tyr | Ser | Glu |
| Arg 705 | Leu | Met | Thr | Leu | Ala 710 | Gly | Val | Tyr | Gly | Phe 715 | Trp | Lys | Tyr | Val | Ser 720 |
| Lys | Leu | Glu | Arg | Arg 725 | Glu | Thr | Arg | Arg | Tyr 730 | Leu | Glu | Met | Phe | Tyr 735 | Ile |
| Leu | Lys | Phe | Arg 740 | Asp | Leu | Ala | Asn | Ser 745 | Val | Pro | Leu | Ala | Thr 750 | Asp | Glu |
| Glu | Pro | Ser 755 | Thr | Thr | Asp | Ala | Val 760 | Ala | Thr | Phe | Arg | Gly 765 | Pro | | |

DNA SEQUENCES AND PLASMIDS FOR THE PREPARATION OF SUGAR BEET WITH CHANGED SUCROSE CONCENTRATION

FIELD OF THE INVENTION

The present invention relates to DNA sequences and plasmids, containing these DNA sequences, which by integration into the genome of a sugar-beet plant, changes the sugar metabolism of the plant to be changed. The invention also relates to transgenic plants formed with the help of these sequences.

BACKGROUND OF THE INVENTION

Sucrose is of central importance for the plant and serves many functions. For the long distance transport of photoassimilates and/or energy between various organs in plants, sucrose is almost exclusively used. The sucrose, which is transported in a specific heterotrophic organ, determines the growth and the development of this organ. Thus it is known, e.g. from EP 442 592, that transgenic plants, in which the transport away of the sucrose from the exporting leaves is inhibited by expression of an apoplastic invertase, shows a strong reduction in the growth of e.g. roots or tubers in the case of potato plants. For tobacco plants, the principal importance of sucrose as the central function for the long distance transport of energy carriers within the plant is described (von Schaewen et al, 1990, EMBO J 9: 3033–3044).

Further it is also known from EP 455 316 that DNA sequences present on plasmids, after introduction in a plant genome of a potato plant can affect the starch biosynthesis as well altering the amount and composition of the protein in the potato tubers.

While it has known that a reduction of the amount of sucrose imported in the heterotrophic organs, such as tubers and seeds, leads to loss of yield, it is not known whether an increase in the amount of sucrose in the photosynthetically active parts of the plant, mainly the leaves, leads to a better supply of heterotrophic organs and thus to an increase in yield.

Besides sucrose and/or the hexoses, glucose and fructose, derived from sucrose, have the property of protection of plants against frost damage at low temperatures. Frost damage is one of the main limiting factors in agricultural productivity in the northern hemisphere. Temperatures below freezing lead to the formation of ice crystals. Since the growing ice crystals consist of pure water, water is extracted from the cells as the temperature falls.

This dehydration has at least two potential damaging results:

1. All dissolved substances within a cell are strongly concentrated and the cell contracts following the loss of water. Highly concentrated salts and organic acids lead to membrane damage.
2. With rehydration from dew, the previously contracted cells reexpand. The cell membrane also expands again. The volume expansion puts a heavy mechanical load on the membrane.

It is thus clear that a freezing/dew cycle can lead to severe membrane damage of the cells and thus to damage to the plant.

SUMMARY OF THE INVENTION

It thus appears worth trying to hinder the freezing. One possible strategy is the increased formation of osmotically active substances in the cytosol of plant cells. This should lead to a lowering of the freezing point. Osmotically active substances include sucrose and/or the two hexoses derived from sucrose.

The increased formation of sucrose and/or the two hexoses at low temperatures is desirable in the growing plant. Another situation can exist in the harvested parts of a plant, especially in storage.

In relation to the economic aspects, sucrose thus possesses two especially important functions:
1. as the transport form for the distant transport of photoassimilates,
2. as an osmotically active substance with the desirable activity of lowering the freezing point in intact, growing plants.

The biosynthesis pathways for the formation of sucrose, either from the primary photosynthesis products (in the leaf) or by breakdown of starch (in the storage organs e.g. of potatoes), are known.

It is however, not known how and in what way changes of the carbohydrate concentration in sugar beet can be achieved since it is not possible to use even very similar genes, such as for example genes that code for a sucrose synthase, ADP-glucose pyrophosphorylase or sucrose phosphate synthase of the potato with satisfactory success for the preparation of sugar beet with changed sucrose concentration. An exact analysis and determination of the DNA sequences or sequence fragments for the sugar beet is thus required.

To change the sugar concentration in sugar beet, DNA sequences are now provided which code for the small and large subunit of the ADP glucose pyrophosphorylase, the sucrose synthase and the sucrose phosphate synthase of sugar beet (Seq. ID No 1–8).

DETAILED DESCRIPTION OF THE INVENTION

The DNA sequences (Seq. ID No. 1–4) can be introduced into plasmids and in this way combined with steering elements for expression in eukaryotic cells. Such steering elements are, on the one hand, transcription promoters and, on the other hand, transcription terminators. Each plasmid comprises:

a) a suitable promoter which ensures that the coding sequence meets a suitable time point or in the specified developments in the transgenic plant or in determined genes of transgenic plants;

b) at least a coding sequence for sugar beet that
   i) is so coupled to the promoter that the formation of an RNA is allowed which is into a protein, whereby the protein demonstrates an enzymatic activity which leads to a change of the sucrose concentration in the plant, or
   ii) which is so coupled to the promoter that the coding part is read, which leads to the formation of a so-called anti-sense RNA which under-expresses the formation of the protein coded from an endogenous gene in the plant, that is involved in the sucrose biosynthesis; and c) A non-coding termination sequence that contains the signal for the termination and polyadenylation of the transcript.

The coding sequences named under b) are the sequences that code for the large and small subunit of the ADP glucose pyrophosphorylase, for the sucrose phosphate synthase and for the sucrose synthase of sugar beet.

The large subunit of the ADP-glucose-pyrophosphorylase has following nucleotide sequence (Seq. ID Nos. 1 and 2):

```
CAAAAGAAAA ACTTCCCATT TCTACTTCTT TGCACAATAT AATTTCCCAC 0050

CAATTTTTCT TTAAATTTCT CACTTTCATT TAATCAGTTT TCAGCAACAT 0100

TCTGATACTC GACAACCCAC TTTCTGTTCT CCCAAGATTC CAAACCTCTG 0150

ATTCTCATTC CACTAATATT TTTGCTTATT TTTTTTCTGG ATTTAAAGAA 0200
```

```
AAGCT ATG GAT GCA AGT GCA GCA GCC ATA AAT GTC AAT GCC CAT        0244
      Met Asp Ala Ser Ala Ala Ala Ile Asn Val Asn Ala His
                    5                       10

TTA ACA GAA GTT GGA AAG AAA CGT TTT TTA GGA GAG AGA ATC AGT      0289
Leu Thr Glu Val Gly Lys Lys Arg Phe Leu Gly Glu Arg Ile Ser
        15                  20                  25

CAA AGT TTG AAG GGT AAA GAT CTG AGA GCT CTG TTT TCA AGA ACT      0334
Gln Ser Leu Lys Gly Lys Asp Leu Arg Ala Leu Phe Ser Arg Thr
        30                  35                  40

GAG AGC AAG GGT AGA AAT GTC AAT AAA CCT GGG GTT GCA TTT TCT      0379
Glu Ser Lys Gly Arg Asn Val Asn Lys Pro Gly Val Ala Phe Ser
        45                  50                  55

GTT CTC ACC TCA GAT TTT AAT CAA AGT GTT AAA GAA TCT TTG AAA      0424
Val Leu Thr Ser Asp Phe Asn Gln Ser Val Lys Glu Ser Leu Lys
        60                  65                  70

TAT GAG CCA GCA TTA TTT GAA TCT CCA AAA GCT GAC CCA AAA AAT      0469
Tyr Glu Pro Ala Leu Phe Glu Ser Pro Lys Ala Asp Pro Lys Asn
        75                  80                  85

GTG GCT GCA ATT GTG CTG GGT GGT GGT GCT GGG ACT ACT CTC TTT      0514
Val Ala Ala Ile Val Leu Gly Gly Gly Ala Gly Thr Arg Leu Phe
        90                  95                  100

CCT CTT ACT AGC AGG AGA GCT AAG CCA GCA GTG CCA ATT GGA GGG      0559
Pro Leu Thr Ser Arg Arg Ala Lys Pro Ala Val Pro Ile Gly Gly
        105                 110                 115

TGT TAC AGG CTG ATT GAT GTG CCT ATG AGC AAC TGC ATC AAC AGT      0604
Cys Tyr Arg Leu Ile Asp Val Pro Met Ser Asn Cys Ile Asn Ser
        120                 125                 130

GGC ATT AGA AAG ATT TTC ATT CTT ACC CAG TTC AAT TCG TTT TCG      0649
Gly Ile Arg Lys Ile Phe Ile Leu Thr Gln Phe Asn Ser Phe Ser
        135                 140                 145

CTT AAT CGT CAT CTT GCT CGA ACC TAT AAT TTT GGA GAT GGT GTG      0694
Leu Asn Arg His Leu Ala Arg Thr Tyr Asn Phe Gly Asp Gly Val
        150                 155                 160

AAT TTT GGG GAT GGC TTT GTG GAG GTT TTT GCT GCT ACA CAA ACA      0739
Asn Phe Gly Asp Gly Phe Val Glu Val Phe Ala Ala Thr Gln Thr
        165                 170                 175
CCT GGA GAA TCA GGA AAG AAA TGG TTC CAG GGC ACC GCT GAT GCA      0784
Pro Gly Glu Ser Gly Lys Lys Trp Phe Gln Gly Thr Ala Asp Ala
        180                 185                 190

GTA AGA CAG TTT TTC TGG GCA TTT GAG GAT TCC AAA TCC AAG GAT      0829
Val Arg Gln Phe Phe Trp Ala Phe Glu Asp Ser Lys Ser Lys Asp
        195                 200                 205

GTC GAG CAT ATA GTT ATT TTA TCC GGT GAT CAT CTT TAC CGA ATG      0874
Val Glu His Ile Val Ile Leu Ser Gly Asp His Leu Tyr Arg Met
        210                 215                 220

GAT TAC ATG AGT TTT TGG CAG AAG CAC ATT GAC ACC AAT GCT GAT      0919
Asp Tyr Met Ser Phe Trp Gln Lys His Ile Asp Thr Asn Ala Asp
        225                 230                 235

ATT ACA GTG TCA TGC ATA CCC ATG GAT GAC AGC CGT GCA TCG GAT      0964
Ile Thr Val Ser Cys Ile Pro Met Asp Asp Ser Arg Ala Ser Asp
        240                 245                 250

TAT GGG CTG ATG AAG ATT GAT CAC ACT GGA CGC ATT GTC CAT TTT      1009
Tyr Gly Leu Met Lys Ile Asp His Thr Gly Arg Ile Val His Phe
        255                 260                 265
```

```
GCA GAA AAA CCC AAG GGT TCT GAT CTA ACA GCA ATG CAA GTA GAT  1054
Ala Glu Lys Pro Lys Gly Ser Asp Leu Thr Ala Met Gln Val Asp
    270             275             280

ACA ACT GTT CTT GGG CTC TCT GAC CTT GAA GCT ATG TCA AAT CCA  1099
Thr Thr Val Leu Gly Leu Ser Asp Leu Glu Ala Met Ser Asn Pro
    285             290             295

TAT ATT GCA TCA ATG GGT GTT TAT GTC TTT CGA ACG GAT GTT CTT  1144
Tyr Ile Ala Ser Met Gly Val Tyr Val Phe Arg Thr Asp Val Leu
    300             305             310

ATG GAG CTT CTC AAT CGA AAA TAC CCT TCA AGC AAT GAT TTT GGC  1189
Met Glu Leu Leu Asn Arg Lys Tyr Pro Ser Ser Asn Asp Phe Gly
    315             320             325

TCT GAG ATT ATT CCT TCA GCT GTA GGA GAG TCT AAT GTT CAG GCA  1234
Ser Glu Ile Ile Pro Ser Ala Val Gly Glu Ser Asn Val Gln Ala
    330             335             340

TAT CTA TTT AAT GAC TAC TGG GAG GAT ATC GGA ACC ATA AAG TCT  1279
Tyr Leu Phe Asn Asp Tyr Trp Glu Asp Ile Gly Thr Ile Lys Ser
    345             350             355

TTC TTT GAT TCC AAT TTG GCC CTT ACA CAA CAG CCT CCC AAG TTT  1324
Phe Phe Asp Ser Asn Leu Ala Leu Thr Gln Gln Pro Pro Lys Phe
    360             365             370

GAA TTC TAC GAT CCA AAA ACA CCT TTT TAT ACA TCT GCA AGA TTT  1361
Glu Phe Tyr Asp Pro Lys Thr Pro Phe Tyr Thr Ser Ala Arg Phe
    375             380             385

CTG CCT CCT ACA AAA GTC GAC AGG TGC AAG ATT GTC GAT TCC ATT  1414
Leu Pro Pro Thr Lys Val Asp Arg Cys Lys Ile Val Asp Ser Ile
    390             395             400

GTA TCC CAT GGT TGT TTT CTA CAG GAG TCT AGC ATC CAA CAT TCC  1454
Val Ser His Gly Cys Phe Leu Gln Glu Ser Ser Ile Gln His Ser
    405             410             415

ATT GTT GGT GTT CGC TCA AGA TTA GAG TCC GGG GTT GAG TTC CAG  1504
Ile Val Gly Val Arg Ser Arg Leu Glu Ser Gly Val Glu Phe Gln
    420             425             430

GAC ACC ATG ATG ATG GGC GCA GAT TAC TAT CAA ACT GAA TCA CAA  1549
Asp Thr Met Met Met Gly Ala Asp Tyr Tyr Gln Thr Glu Ser Glu
    435             440

ATT GCT TCT CTG CTT GCT GAG GGA AAG GTT CCT GTT GGT GTC GGA  1594
Ile Ala Ser Leu Leu Ala Glu Gly Lys Val Pro Val Gly Val Gly
    450             455             460

CAG AAT ACC AAA ATA AAG AAT TGC ATA ATT GAC AAG AAC GCC AAA  1639
Gln Asn Thr Lys Ile Lys Asn Cys Ile Ile Asp Lys Asn Ala Lys
    465             470             475

ATT GGA AAA GAT GTG GTA ATC GCA AAC ACG GAT GGT GTT GAG GAA  1884
Ile Gly Lys Asp Val Val Ile Ala Asn Thr Asp Gly Val Glu Glu
    480             485             490

GCA GAT AGA CCA AAT GAA GGC TTT TAC ATC AGG TCG GGC ATT ACC  1729
Ala Asp Arg Pro Asn Glu Gly Phe Tyr Ile Arg Ser Gly Ile Thr
    495             500             505

ATC ATT TTG AAG AAC GCA ACC ATA CAA GAC GGT CTT GTG ATT TAG  1774
Ile Ile Leu Lys Asn Ala Thr Ile Gln Asp Gly Leu Val Ile End
    510             515             520

ATTTAATCAT  AACCTCATTA  GAAAGAAATA  ATTTTGCATG  ATTTCCTTTT   1824

CATGTAACCT  AAACTGGCTA  AACCACGAGG  TTTTCTCATC  TGTATATATA   1874

ATATGTCTAT  AACTATGGAT  AATCTTAATA  AAAAAAAAAA  AAAAAAAAAA   1924

A                                                            1925
```

The small subunit of the ADP-glucose-pyrophosphalase has the following nucleotide sequence (Seq. ID Nos. 3 and 4):

| | | | | | | | | | | | | | | | |
|---|---|---|---|---|---|---|---|---|---|---|---|---|---|---|---|
| | GG | ATA | ACT | GTG | CCA | TCA | ACC | TCC | TCA | AAG | AAC | CTC | CAA | AAT | AGC | 0044 |
| | | Ile | Thr | Val | Pro | Ser | Thr | Ser | Ser | Lys | Asn | Leu | Gln | Asn | Ser | |
| | | | | | 5 | | | | | 10 | | | | | | |
| CTC | GCA | TTC | TCC | TCT | TCT | TCT | CTC | TCC | GGC | GAC | AAA | ATT | CAA | ACG | 0089 |
| Leu | Ala | Phe | Ser | Ser | Ser | Ser | Leu | Ser | Gly | Asp | Lys | Ile | Gln | Thr | |
| 15 | | | | 20 | | | | | 25 | | | | | | |
| ACG | TCA | TTT | CTC | AAC | CGC | CGA | TAT | TGT | AGA | ATC | TCT | TCT | AGA | GCT | 0134 |
| Thr | Ser | Phe | Leu | Asn | Arg | Arg | Tyr | Cys | Arg | Ile | Ser | Ser | Arg | Ala | |
| 30 | | | | | 35 | | | | 40 | | | | | | |
| CCG | AAT | GTT | GTC | TCT | CCC | AAA | GCT | GTT | TCT | GAT | TCT | AAG | AAT | TCG | 0179 |
| Pro | Ile | Val | Val | Ser | Pro | Lys | Ala | Val | Ser | Asp | Ser | Lys | Asn | Ser | |
| 45 | | | | | 50 | | | | 55 | | | | | | |
| CAG | ACT | TGT | CTT | GAC | CCT | GAA | GCC | AGC | CGT | AGT | GTT | CTT | GGT | ATT | 0224 |
| Gln | Thr | Cys | Leu | Asp | Pro | Glu | Ala | Ser | Arg | Ser | Val | Leu | Gly | Ile | |
| 60 | | | | | 65 | | | | 70 | | | | | | |
| ATA | CTT | GGA | GGT | GGT | GCT | GGT | ACA | CGT | CTT | TAC | CCG | TTG | ACT | AAG | 0269 |
| Ile | Leu | Gly | Gly | Gly | Ala | Gly | Thr | Arg | Leu | Tyr | Pro | Leu | Thr | Lys | |
| 75 | | | | | 80 | | | | 85 | | | | | | |
| AAG | AGA | GCC | AAA | CCA | GCC | GTG | CCA | CTC | GGT | GCT | AAT | TAT | AGG | CTT | 0314 |
| Lys | Arg | Ala | Lys | Pro | Ala | Val | Pro | Leu | Gly | Ala | Asn | Tyr | Arg | Leu | |
| 90 | | | | | 95 | | | | 100 | | | | | | |
| ATT | GAT | ATC | CCA | GTG | AGC | AAT | TGT | TTG | AAC | AGT | AAT | ATT | TCC | AAA | 0359 |
| Ile | Asp | Ile | Pro | Val | Ser | Asn | Cys | Leu | Asn | Ser | Asn | Ile | Ser | Lys | |
| 105 | | | | | 110 | | | | 110 | | | | | | |
| ATA | TAT | GTT | CTT | ACA | CAA | TTC | AAT | TCT | GCT | TCT | CTG | AAT | CGT | CAT | 0404 |
| Ile | Tyr | Val | Leu | Thr | Gln | Phe | Asn | Ser | Ala | Ser | Leu | Asn | Arg | His | |
| 115 | | | | | 120 | | | | 125 | | | | | | |
| CTT | TCG | CGG | GCA | TAT | GCT | AGC | AAC | ATG | GGA | GGA | TAC | AAA | AAT | GAG | 0449 |
| Leu | Ser | Arg | Ala | Tyr | Ala | Ser | Asn | Met | Gly | Gly | Tyr | Lys | Asn | Glu | |
| 130 | | | | | 135 | | | | 140 | | | | | | |
| GGG | TTT | GTA | GAA | GTT | CTT | GCT | GCT | CAG | CAA | AGT | CCA | GAG | AAT | CCA | 0494 |
| Gly | Phe | Val | Glu | Val | Leu | Ala | Ala | Gln | Gln | Ser | Pro | Glu | Asn | Pro | |
| 145 | | | | | 150 | | | | 155 | | | | | | |
| AAC | TGG | TTT | CAG | GGT | ACA | GCT | GAT | GCT | GTT | AGG | CAA | TAT | CTG | TGG | 0539 |
| Asn | Trp | Phe | Gln | Gly | Thr | Ala | Asp | Ala | Val | Arg | Gln | Tyr | Leu | Trp | |
| 160 | | | | | 165 | | | | 170 | | | | | | |
| CTT | TTC | GAA | GAG | CAC | AAT | GTT | CTT | GAG | TAC | TTG | ATT | CTT | GCT | GGT | 0584 |
| Leu | Phe | Glu | Glu | His | Asn | Val | Leu | Glu | Tyr | Leu | Ile | Leu | Ala | Gly | |
| 175 | | | | | 180 | | | | 185 | | | | | | |
| GAC | CAT | TTG | TAT | CGA | ATG | GAT | TAT | GAA | AGA | TTT | GTC | CAA | GCT | CAC | 0629 |
| Asp | His | Leu | Tyr | Arg | Met | Asp | Tyr | Glu | Arg | Phe | Val | Gln | Ala | His | |
| 190 | | | | | 195 | | | | 200 | | | | | | |
| AGA | GAA | ACT | GAT | GCA | GAC | ATT | ACT | GTT | GCT | GCA | TTG | CCA | ATG | GAT | 0674 |
| Arg | Glu | Thr | Asp | Ala | Asp | Ile | Thr | Val | Ala | Ala | Leu | Pro | Met | Asp | |
| 205 | | | | | 210 | | | | 215 | | | | | | |
| GAA | AAG | CGT | GCT | ACT | GCA | TTT | GGT | TTG | ATG | AAA | ATT | GAT | GAA | GAA | 0719 |
| Glu | Lys | Arg | Ala | Thr | Ala | Phe | Gly | Leu | Met | Lys | Ile | Asp | Glu | Glu | |
| 220 | | | | | 225 | | | | 230 | | | | | | |
| GGA | AGA | ATT | ATT | GAG | TTT | GCC | GAG | AAA | CCG | AAA | GGA | GAA | CAA | TTG | 0764 |
| Gly | Arg | Ile | Ile | Glu | Phe | Ala | Glu | Lys | Pro | Lys | Gly | Glu | Gln | Leu | |
| 235 | | | | | 240 | | | | 245 | | | | | | |
| AAA | GCT | ATG | AAG | GTT | GAT | ACC | ACA | ATC | CTG | GGT | CTG | GAC | GAT | GAG | 0809 |
| Lys | Ala | Met | Lys | Val | Asp | Thr | Thr | Ile | Leu | Gly | Leu | Asp | Asp | Glu | |
| 250 | | | | | 255 | | | | 260 | | | | | | |
| AGA | GCA | AAA | GAA | ATG | CCA | TTC | ATA | GCC | AGC | ATG | GGC | ATA | TAT | GTT | 0854 |
| Arg | Ala | Lys | Glu | Met | Pro | Phe | Ile | Ala | Ser | Met | Gly | Ile | Tyr | Val | |
| 265 | | | | | 270 | | | | 275 | | | | | | |
| ATT | AGC | AAA | GAT | GTA | ATG | CTT | ATT | CTG | CTT | CGG | GAG | CAA | TTT | CCT | 0899 |
| Ile | Ser | Lys | Asp | Val | Met | Leu | Ile | Leu | Leu | Arg | Glu | Gln | Phe | Pro | |
| 280 | | | | | 285 | | | | 290 | | | | | | |
| GGT | GCT | AAT | GAT | TTT | GGA | AGT | GAA | GTT | ATT | CCA | GGC | GCC | ACT | TCC | 0944 |
| Gly | Ala | Asn | Asp | Phe | Gly | Ser | Glu | Val | Ile | Pro | Gly | Ala | Thr | Ser | |
| 295 | | | | | 300 | | | | 305 | | | | | | |

```
ATA GGG TTG AGA GTC CAA GCT TAT TTG TAT GAT GGT TAC TGG GAG  0989
Ile Gly Leu Arg Val Gln Ala Tyr Leu Tyr Asp Gly Tyr Trp Glu
310                 315                 320

GAT ATT GGT ACC ATT GAA GCT TTT TAC AAT GCT AAC TTG GGA ATC  1034
Asp Ile Gly Thr Ile Glu Ala Phe Tyr Asn Ala Asn Leu Gly Ile
325                 330                 335

ACC AAA AAG CCG GTG CCA GAT TTT AGC TTC TAT GAT CGT TCA TCT  1079
Thr Lys Lys Pro Val Pro Asp Phe Ser Phe Tyr Asp Arg Ser Ser
340                 345                 350

CCA ATT TAT ACA CAA CCT CGG TAT TTG CCT CCT TCA AAG ATG CTT  1124
Pro Ile Tyr Thr Gln Pro Arg Tyr Leu Pro Pro Ser Lys Met Leu
355                 360                 365

GAT GCT GAT ATA ACT GAC AGC GTC ATC GGT GAA GGC TGT GTT ATT  1169
Asp Ala Asp Ile Thr Asp Ser Val Ile Gly Glu Gly Cys Val Ile
370                 375                 380

AAG AAC TGT AAG ATT CAT CAT TCT GTT ATC GGA CTT CGA TCT TGT  1214
Lys Asn Cys Lys Ile His His Ser Val Ile Gly Leu Arg Ser Cys
385                 390                 395

ATC TCG GAG GGT GCA ATC ATT GAG GAC ACA CTG TTG ATG GGA GCT  1259
Ile Ser Glu Gly Ala Ile Ile Glu Asp Thr Leu Leu Met Gly Ala
400                 405                 410

GAT TAT TAT GAG ACT GAT GCT GAT CGG AAA TTC CTG GCT GCT AAG  1304
Asp Tyr Tyr Glu Thr Asp Ala Asp Arg Lys Phe Leu Ala Ala Lys
415                 420                 425

GGT AGT GTA CCT ATT GGA ATT GGG AAT GCA CGT ATT GGG GAT GAT  1349
Gly Ser Val Pro Ile Gly Ile Gly Asn Ala Arg Ile Gly Asp Asp
430                 435                 440

GTC AAG ATT ATC AAC AGT GAC AAT GTA CAA GAA GCA GCA AGA GAA  1394
Val Lys Ile Ile Asn Ser Asp Asn Val Gln Glu Ala Ala Arg Glu
445                 450                 455

ACA GAC GGA TAC TTC ATA AAG AGC GGA ATA GTC ACT ATA ATC AAG  1439
Thr Asp Gly Tyr Phe Ile Lys Ser Gly Ile Val Thr Ile Ile Lys
460                 465                 470

GAC GCC ATG ATT CCA AGT GGA ACT GTA ATC TAG AAATGGAGCA       1482
Asp Ala Met Ile Pro Ser Gly Thr Val Ile End
475                 480             485

TATAATAAAT ATCACTGCCT ATTTACAGTA CCTATCTGAG TCTCCCACCA       1532

TGACCCTTTG ATTCAATCTT TTAGTTATGT AAATATTTTT GGCTTTTGCG       1582

ATTTTGCCAT AAATTTGAAG AAGCGAGGAT TCAGGGACGA TAGTGCTATG       1632

AATTGGAAGA AAGGATTTGG GGGATATCTT TGTAAAGACA TTTTGACTAC       1682

TGGGCACTAA AAATTTGGTA ATGCTATACC AAAATATATA AAAGATCTT        1732

GCTGGGTTTT GGTAAAAAAA AAAAAAAAAA A                           1763
```

The sucrose phosphate—synthase has the following nucleotide sequence (Seq. ID Nos. 5 and 6):

```
GGGCTGCAGG GAAGCTCTGA ACTTCAAAA ATG GCG GGA AAT GAT           0044
                                  Met Ala Gly Asn Asp
                                                    5

TGG ATA AAC AGT TAT TTA GAG GCA ATT CTG GAT GTG GGT CCA GGA  0089
Trp Ile Asn Ser Tyr Leu Glu Ala Ile Leu Asp Val Gly Pro Gly
            10                  15                  20
```

```
                                                    -continued
CTT GAT GAT GCA AAA TCA TCT TTG CTT TTG AGA GAA AGA GGC AGG  0134
Leu Asp Asp Ala Lys Ser Ser Leu Leu Leu Arg Glu Arg Gly Arg
            25              30                          35

TTT AGT CCT ACT CGT TAC TTT GTT GAA GAA GTT ATC ACT GGT TTT  0179
Phe Ser Pro Thr Arg Tyr Phe Val Glu Glu Val Ile Thr Gly Phe
            40              45                          50

GAT GAA ACC GAC CTT CAT CGT TCA TGG GTT CGG GCA CAA GCA ACA  0224
Asp Glu Thr Asp Leu His Arg Ser Trp Val Arg Ala Gln Ala Thr
            55              60                          65

AGG AGT CCT CAA GAG AGG AAT ACT AGA TTG GAG AAC ATG TGT TGG  0269
Arg Ser Pro Gln Glu Arg Asn Thr Arg Leu Glu Asn Met Cys Trp
            70              75                          80

AGA ATT TGG AAT TTG GCT CGT CAG AAG AAG CAG CTT GAG AAT GAA  0314
Arg Ile Trp Asn Leu Ala Arg Gln Lys Lys Gln Leu Glu Asn Glu
            85              90                          95

GAA GCT CAG CGG AAG ACA AAA CGT CGT ATG GAG CTT GAG AGG GGT  0359
Glu Ala Gln Arg Lys Thr Lys Arg Arg Met Glu Leu Glu Arg Gly
            100             105                         110

CGT CGA GAA GCA ACT GCT GAT ATG TCG GAG GAC TTA TCA GAA GGC  0404
Arg Arg Glu Ala Thr Ala Asp Met Ser Glu Asp Leu Ser Glu Gly
            115             120                         125

GAA AAG GAC ATT TCA GCT CAT GGT GAT AGC ACC CGT CCT AGA TTG  0449
Glu Lys Asp Ile Ser Ala His Gly Asp Ser Thr Arg Pro Arg Leu
            130             135                         140

CCA AGA ATA AAT TCT CTT GAT GCT ATG GAG ACA TGG ATT AGT CAA  0494
Pro Arg Ile Asn Ser Leu Asp Ala Met Glu Thr Trp Ile Ser Gln
            145             150                         155

CAA AAG GAA AAA AAA CTC TAC CTT GTT TTG ATA AGT CTT CAT GGT  0539
Gln Lys Glu Lys Lys Leu Tyr Leu Val Leu Ile Ser Leu His Gly
            160             165                         170

TTG ATA CGA GGT GAA AAC ATG GAA CTT GGC CGT GAT TCT GAT ACT  0584
Leu Ile Arg Gly Glu Asn Met Glu Leu Gly Arg Asp Ser Asp Thr
            175             180                         185

GGT GGT CAG GTT AAG TAT GTG GTT GAG CTT GCA AGG GCT CTA GGT  0629
Gly Gly Gln Val Lys Tyr Val Val Glu Leu Ala Arg Ala Leu Gly
            190             195                         200

TCG ATG CCA GGT GTT TAT AGA GTT GAT TTG CTA ACT AGG CAA GTT  0674
Ser Met Pro Gly Val Tyr Arg Val Asp Leu Leu Thr Arg Gln Val
            205             210                         215

TCA TCT CCT GAC GTG GAT TGG AGT TAT GGG GAG CCT ACT GAG ATG  0719
Ser Ser Pro Asp Val Asp Trp Ser Tyr Gly Glu Pro Thr Glu Met
            220             225                         230

CTG AAT CCA AGG GAT TCC AAT GGT TTT GAT GAT GAT GAT GAT GAA  0764
Leu Asn Pro Arg Asp Ser Asn Gly Phe Asp Asp Asp Asp Asp Glu
            235             240                         245

ATG GGA GAG AGT AGT GGT GCT TAC ATT GTT CGT ATA CCA TTT GGG  0809
Met Gly Glu Ser Ser Gly Ala Tyr Ile Val Arg Ile Pro Phe Gly
            250             255                         260

CCG AGG GAT AAG TAT ATC GCA AAA GAA GAG CTT TGG CCC TAT ATT  0854
Pro Arg Asp Lys Tyr Ile Ala Lys Glu Glu Leu Trp Pro Tyr Ile
            265             270                         275

CCT GAA TTT GTT GAT GGT GCT CTA AAC CAC ATA GTT CAA ATG TCC  0899
Pro Glu Phe Val Asp Gly Ala Leu Asn His Ile Val Gln Met Ser
            280             285                         290

AAA GTT TTA GGT GAG CAA ATT GGT AGC GGG GAA ACA GTT TGG CCA  0944
Lys Val Leu Gly Glu Gln Ile Gly Ser Gly Glu Thr Val Trp Pro
            295             300                         305

GTT GCC ATT CAT GGA CAT TAT GCT GAT GCT GGT GAT TCT GCT GCT  0989
Val Ala Ile His Gly His Tyr Ala Asp Ala Gly Asp Ser Ala Ala
            310             315                         320

CTT CTT TCT GGT GGC CTA AAT GTT CCA ATG CTT TTA ACG GGG CAT  1034
Leu Leu Ser Gly Gly Leu Asn Val Pro Met Leu Leu Thr Gly His
            325             330                         335
```

```
TCT CTT GGC CGA GAC AAG TTA GAG CAG CTC CTC AAA CAG GGT CGA 1079
Ser Leu Gly Arg Asp Lys Leu Glu Gln Leu Leu Lys Gln Gly Arg
            340                 345                 350

ATG TCT AAA GAT GAC ATA AAC AAT ACA TAC AAA ATA ATG CGT AGG 1124
Met Ser Lys Asp Asp Ile Asn Asn Thr Tyr Lys Ile Met Arg Arg
            355                 360                 365

ATA GAA GCC GAA GAG TTA TCA CTT GAT GCC TCT GAG ATA GTC ATA 1169
Ile Glu Ala Glu Glu Leu Ser Leu Asp Ala Ser Glu Ile Val Ile
            370                 375                 380

ACT AGT ACA AGA CAA GAA ATA GAA GAG CAA TGG CAC CTC TAT GAT 1214
Thr Ser Thr Arg Gln Glu Ile Glu Glu Gln Trp His Leu Tyr Asp
            385                 390                 395

GGG TTT GAT CCT GTG CTA GAA CGT AAA CTC CGT GCT AGG ATG AAG 1259
Gly Phe Asp Pro Val Leu Glu Arg Lys Leu Arg Ala Arg Met Lys
            400                 405                 410

CGT GGT GTA AGC TGT TAT GGA AGG TTC ATG CCC CGG ATG GTT GTT 1304
Arg Gly Val Ser Cys Tyr Gly Arg Phe Met Pro Arg Met Val Val
            415                 420                 425

ATT CCT CCT GGA ATG GAA TTC AAT CAT ATT GTT CCA CAT GAG GGT 1349
Ile Pro Pro Gly Met Glu Phe Asn His Ile Val Pro His Glu Gly
            430                 435                 440

GAT ATG GAT GGT GAA ACA GAA GAA ACT GAA GAG CAT CCT ACA TCA 1394
Asp Met Asp Gly Glu Thr Glu Glu Thr Glu Glu His Pro Thr Ser
            445                 450                 455

CCT GAT CCA CCT ATC TGG GCT GAG ATT ATG CGC TTC TTT TCT AAA 1439
Pro Asp Pro Pro Ile Trp Ala Glu Ile Met Arg Phe Phe Ser Lys
            460                 465                 470

CCA AGG AAG CCA ATG ATA CTT GCC CTT GCT AGG CCT GAC CCG AAG 1484
Pro Arg Lys Pro Met Ile Leu Ala Leu Ala Arg Pro Asp Pro Lys
            475                 480                 485

AAG AAT ATC ACG ACT TTG GTC AAA GCA TTT GGA GAA TGC CGT CCA 1529
Lys Asn Ile Thr Thr Leu Val Lys Ala Phe Gly Glu Cys Arg Pro
            490                 495                 500

CTA AGG GAG CTA GCT AAT CTT ACT CTT ATA ATG GGT AAC CGA GAT 1574
Leu Arg Glu Leu Ala Asn Leu Thr Leu Ile Met Gly Asn Arg Asp
            505                 510                 515

GGT ATT GAC GAG ATG TCA AGC ACC AGT TCT TCA GTT CTC CTG TCA 1619
Gly Ile Asp Glu Met Ser Ser Thr Ser Ser Ser Val Leu Leu Ser
            520                 525                 530

GTG CTT AAG CTA ATT GAT CAA TAC GAC CTT TAT GGT CAA GTA GCA 1664
Val Leu Lys Leu Ile Asp Gln Tyr Asp Leu Tyr Gly Gln Val Ala
            535                 540                 545

TAC CCC AAA CAT CAC AAG CAA GCT GAT GTT CCT GAG ATT TAT CGT 1709
Tyr Pro Lys His His Lys Gln Ala Asp Val Pro Glu Ile Tyr Arg
            550                 555                 600

TTG GCA GCA AAG ACA AAG GGA GTC TTT ATT AAT CCA GCT TTT ATT 1754
Leu Ala Ala Lys Thr Lys Gly Val Phe Ile Asn Pro Ala Phe Ile
            605                 610                 615

GAG CCA TTT GGG CTG ACT CTA ATA GAG GCA GCA GCT CAT GGT TTA 1799
Glu Pro Phe Gly Leu Thr Leu Ile Glu Ala Ala Ala His Gly Leu
            620                 625                 630

CCG ATG GTT GCT ACG AAA AAT GGA GGC CCT GTT GAT ATC CAG AGG 1844
Pro Met Val Ala Thr Lys Asn Gly Gly Pro Val Asp Ile Gln Arg
            635                 640                 645

GTC CTT GAT AAT GGT CTT CTT GTG GAT CCT CAT GAG CAG CAG TCT 1889
Val Leu Asp Asn Gly Leu Leu Val Asp Pro His Glu Gln Gln Ser
            650                 655                 660

ATT GCT ACT GCT TTG CTG AAG CTT GTT GCT GAT AAG CAA CTA TGG 1934
Ile Ala Thr Ala Leu Leu Lys Leu Val Ala Asp Lys Gln Leu Trp
            665                 670                 675
```

| | | | | | | | | | | | | | | |
|---|---|---|---|---|---|---|---|---|---|---|---|---|---|---|
| ACA | AAA | TGC | CAG | CAA | AAT | GGA | CTG | AAA | AAT | ATT | CAT | CTC | TAC | TCT 1979 |
| Thr | Lys | Cys | Gln | Gln 680 | Asn | Gly | Leu | Lys | Asn 685 | Ile | His | Leu | Tyr | Ser 690 |
| TGG | CCA | GAG | CAT | TCG | AAG | ACA | TAC | TCA | TCT | CGA | ATA | GCC | AGT | TCG 2024 |
| Trp | Pro | Glu | His | Ser 695 | Lys | Thr | Tyr | Leu | Ser 700 | Arg | Ile | Ala | Ser | Ser 705 |
| AGA | CAA | AGG | CAA | CCA | CAG | TGG | CAA | AGA | AGT | AGT | GAT | GAA | GGG | CTT 2069 |
| Arg | Gln | Arg | Gln | Pro 710 | Gln | Trp | Gln | Arg | Ser 715 | Ser | Asp | Glu | Gly | Leu 720 |
| GAC | AAT | CAA | GAG | CCT | GAA | TCT | CCA | AGT | GAT | TCT | TTA | AGA | GAT | ATA 2114 |
| Asp | Asn | Gln | Glu | Pro 725 | Glu | Ser | Pro | Ser | Asp 730 | Ser | Leu | Arg | Asp | Ile 735 |
| AAG | GAT | ATA | TCT | CTA | AAC | CTT | GAA | GTT | CTC | GTT | AGA | CCG | GAG | AAA 2159 |
| Lys | Asp | Ile | Ser | Leu 740 | Asn | Leu | Glu | Val | Leu 745 | Val | Arg | Pro | Glu | Lys 750 |
| AGG | GTG | AAG | ACG | TTG | AAA | ATC | TTG | GGA | TTG | ATG | ACA | AAA | GCA | AAT 2204 |
| Arg | Val | Lys | Thr | Leu 755 | Lys | Ile | Leu | Gly | Leu 760 | Met | Thr | Lys | Ala | Asn 765 |
| TCG | AGA | ATG | CTG | TTA | TGT | TCA | TGG | TCT | AAT | GGT | CTC | CAT | AAG | ATG 2249 |
| Ser | Arg | Met | Leu | Leu 770 | Cys | Ser | Trp | Ser | Asn 775 | Gly | Val | His | Lys | Met 780 |
| CTT | CGG | AAG | GCT | CGG | TTC | TCT | GAC | AAA | GTA | GAT | CAG | GCT | TCT | AGT 2294 |
| Leu | Arg | Lys | Ala | Arg 785 | Phe | Ser | Asp | Lys | Val 790 | Asp | Gln | Ala | Ser | Ser 795 |
| AAA | TAT | CCA | GCA | TTT | AGG | AGG | AGA | AAA | CTT | ATA | TAT | GTT | ATT | GCT 2339 |
| Lys | Tyr | Pro | Ala | Phe 800 | Arg | Arg | Arg | Lys | Leu 805 | Ile | Tyr | Val | Ile | Ala 810 |
| GTA | GAC | GGG | GAT | TAT | GAA | GAT | GGA | CTT | TTT | GAT | ATT | GTT | CGG | AGG 2384 |
| Val | Asp | Gly | Asp | Tyr 815 | Glu | Asp | Gly | Leu | Phe 820 | Asp | Ile | Val | Arg | Arg 825 |
| ATA | TTT | GAT | GCT | GCT | GGC | AAG | GAG | AAG | ATT | GAA | GGT | TCC | ATC | GGG 2429 |
| Ile | Phe | Asp | Ala | Ala 830 | Gly | Lys | Glu | Lys | Ile 835 | Glu | Gly | Ser | Ile | Gly 840 |
| TTT | ATA | TTG | TCA | ACA | TCC | TAT | TCT | ATG | CCC | GAA | ATT | CAG | AAC | TAT 2474 |
| Phr | Ile | Leu | Ser | Thr 845 | Ser | Tyr | Ser | Met | Pro 850 | Glu | Ile | Gln | Asn | Tyr 855 |
| TTG | CTA | TCA | AAA | GGC | TTC | AAT | CTT | CAT | GAT | TTT | GAT | GCA | TAT | ATA 2519 |
| Leu | Leu | Ser | Lys | Gly 860 | Phe | Asn | Leu | His | Asp 865 | Phe | Asp | Ala | Tyr | Ile 870 |
| TGC | AAC | AGT | GGG | AGT | GAG | TTG | TAC | TAT | TCA | TCT | TTG | AAC | TCA | GAG 2564 |
| Cys | Asn | Ser | Gly | Ser 875 | Glu | Leu | Tyr | Tyr | Ser 880 | Ser | Leu | Asn | Ser | Glu 885 |
| GAG | AGT | AAT | ATT | ATA | GCA | GAT | TCA | GAT | TAC | CAT | TCA | CAC | ATA | GAG 2609 |
| Glu | Ser | Asn | Ile | Ile 890 | Ala | Asp | Ser | Asp | Tyr 895 | His | Ser | His | Ile | Glu 900 |
| TAC | AGA | TGG | GGT | GGA | GAA | GGC | CTT | AGA | AGG | ACT | TTG | CTT | CGC | TGG 2654 |
| Tyr | Arg | Trp | Gly | Gly 905 | Glu | Gly | Leu | Arg | Arg 910 | Thr | Leu | Leu | Arg | Trp 915 |
| GCA | GCT | TCC | ATC | ACA | GAA | AAA | AAT | GGT | GAA | AAC | GAA | GAA | CAG | GTT 2699 |
| Ala | Ala | Ser | Ile | Thr 920 | Glu | Lys | Asn | Gly | Glu 925 | Asn | Glu | Glu | Gln | Val 930 |
| ATT | ACT | GAA | GAT | GAA | GAA | GTT | TCT | ACG | GGT | TAT | TGC | TTT | GCG | TTT 2744 |
| Ile | Thr | Glu | Asp | Glu 935 | Glu | Val | Ser | Thr | Gly 940 | Tyr | Cys | Phe | Ala | Phe 945 |
| AAA | ATA | AAG | AAC | CAA | AAT | AAG | GTT | CCC | CCT | ACG | AAG | GAG | CTC | CGC 2789 |
| Lys | Ile | Lys | Asn | Gln 950 | Asn | Lys | Val | Pro | Pro 955 | Thr | Lys | Glu | Leu | Arg 960 |
| AAG | TCA | ATG | AGG | ATT | CAA | GCT | CTT | CGT | TGC | CAT | GTG | ATT | TAC | TGT 2834 |
| Lys | Ser | Met | Arg | Ile 965 | Gln | Ala | Leu | Arg | Cys 970 | His | Val | Ile | Tyr | Cys 975 |
| CAG | AAC | GGA | TCT | AAA | ATG | AAT | GTG | ATT | CCA | GTA | CTA | GCA | TCC | CGT 2879 |
| Gln | Asn | Gly | Ser | Lys 980 | Met | Asn | Val | Ile | Pro 985 | Val | Leu | Ala | Ser | Arg 990 |

```
TCT CAA GCC CTC AGG TAT CTT TAT GTT CGT TGG GGA GTT GAG TTG    2924
Ser Gln Ala Leu Arg Tyr Leu Tyr Val Arg Trp Gly Val Glu Leu
            995                 1000                    1005

TCG AAG ATG GTT GTC TTT GTT GGA GAA TGT GGT GAC ACA GAT TAT    2969
Ser Lys Met Val Val Phe Val Gly Glu Cys Gly Asp Thr Asp Tyr
           1010                 1015                    1020

GAA GGC TTG CTT GGC GGG GTC CAT AAA ACC GTA ATA CTG AAG GGA    3014
Glu Gly Leu Leu Gly Gly Val His Lys Thr Val Ile Leu Lys Gly
           1025                 1030                    1035

GTC TCC AAC ACT GCT TTA AGG TCT CTC CAT GCC AAC AGA AGT TAC    3059
Val Ser Asn Thr Ala Leu Arg Ser Leu His Ala Asn Arg Ser Tyr
           1040                 1045                    1050

CCT CTT TCA CAT GTC GTG TCG CTT GAC AGC CCC AAT ATT GGC GAG    3104
Pro Leu Ser His Val Val Ser Leu Asp Ser Pro Asn Ile Gly Glu
           1055                 1060                    1065

GTG AGC AAA GGG TGC AGC AGC TCC GAG ATC CAG TCC ATC GTC ACA    3149
Val Ser Lys Gly Cys Ser Ser Ser Glu Ile Gln Ser Ile Val Thr
           1070                 1075                    1080

AAA CTC TCC AAA GCT TAA TCAGATATCT GCTGCTTTCT TTTGGGTAAG       3197
Lys Leu Ser Lys Ala End
               1085

CAAGGTTTCA TCTTATATGA TTATATCATA AGATACTATA TAAGCACCTT         3247

ATTGGTAAGT CAGTCCCATA ATAATAATGT ACTTCAGAAC CACAATACTT         3297

AAAAGTTGGT TCAGTAGTGA TTAGTCTCAT AATAATCATA TAATTACACA         3347

TCCGCTGTTA ACTAGTGGTA ATATCTAAGC TCAACAATAA AGATGTAAAA         3397

TGCTAGTATG GAAATGAATT GCTAGCTGTT GATCTCTTTC CCTTTATTCT         3447

GTATTATTTC TTTCCTCATC TCATGTAAAA ACAATTTTCT GAAGGTGTAC         3497

AGTTTTTTCC CCTTATATAT CTGTATTATT TCTACTATTT TTTGTTTGTA         3547

AGAATATCCT CTCATCGAGG AGTGATAATT AAATAACCGG CTTGCTAAAT         3597

ATAAAGCTTA TTCGAGTTAA AAAAAAAAAA AAAAAAAA                      3635
```

The sucrose-synthase has the following nucleotide sequence (Seq. ID Nos. 7 and 8):

```
  CT GCA GGA GGG AAA CAA ATT CTT AGC GAT GGC CCG TTT AGC GAA    0044
     Ala Gly Gly Lys Gln Ile Leu Ser Asp Gly Pro Phe Ser Glu
                  5                 10

GTT CTT AGG TCT GCT CAG GAA GCA ATA GTT GTT CCT CCC TTT GTT    0089
Val Leu Arg Ser Ala Gln Glu Ala Ile Val Val Pro Pro Phe Val
 15              20                  25

GCT ATA GCA GTC CGT CCA AGA CCT GGA GTT TGG GAA TAT GTT CGT    0134
Ala Ile Ala Val Arg Pro Arg Pro Gly Val Trp Glu Tyr Val Arg
 30              35                  40

GTT AAT GTC TCT GAA CTG AAT GTG GAG CAG CTA ACT GTG TCT GAG    0179
Val Asn Val Ser Glu Leu Asn Val Glu Gln Leu Thr Val Ser Glu
 45              50                  55

TAT CTC CAT TTC AAG GAA GAA CTT GTG GAT GGA AAG GCT GAT GAC    0224
```

```
                Tyr  Leu  His  Phe  Lys  Glu  Glu  Leu  Val  Asp  Gly  Lys  Ala  Asp  Asp
                 60                      65                  70

CAC TAT GTG CTT GAG CTT GAT TTC GAG CCT TTT AAT GAA TCA GTT    0269
His Tyr Val Leu Glu Leu Asp Phe Glu Pro Phe Asn Glu Ser Val
 75                  80                  85

CCA CGT CCA ACT CGC TCT TCA TCA ATT GGT AAT GGT GTT CAG TTC    0314
Pro Arg Pro Thr Arg Ser Ser Ser Ile Gly Asn Gly Val Gln Phe
 90                  95                 100

CTC AAT CGG CAC CTG TCA TCA AGC ATG TTC TGC AAC AAA GAT TGC    0359
Leu Asn Arg His Leu Ser Ser Ser Met Phe Cys Asn Lys Asp Cys
105                 110                 115

TTG GAG CCG TTA CTT GAT TTT CTT AGA GTG CAC AAA CAT AAA GGA    0404
Leu Glu Pro Leu Leu Asp Phe Leu Arg Val His Lys His Lys Gly
120                 125                 130

GTT GTC ATG ATG TTG AAT GAT CGG ATA CAG ACT ATC CAG CGT CTT    0449
Val Val Met Met Leu Asn Asp Arg Ile Gln Thr Ile Gln Arg Leu
135                 140                 145

CAG TCT GCA TTG TCT AAA GCT GAG GAT TAT CTT ATC AAA CTT CCA    0494
Gln Ser Ala Leu Ser Lys Ala Glu Asp Tyr Leu Ile Lys Leu Pro
150                 155                 160

GCA GAT ACA CCT TAC TCT GAG TTC GAA TTT GTA ATC CAA GGT ATG    0539
Ala Asp Thr Pro Tyr Ser Gln Phe Glu Phe Val Ile Gln Gly Met
165                 170                 175

GGT TTT GAA AGA GGC TGG GGT GAT ACT GCT GAA AGG GTT CTA GAA    0584
Gly Phe Glu Arg Gly Trp Gly Asp Thr Ala Glu Arg Val Leu Glu
180                 185                 190

ATG ATG CAT CTA CTA CTA GAT ATC CTT CAG GCT CCC GAT CCG TCT    0629
Met Met His Leu Leu Leu Asp Ile Leu Gln Ala Pro Asp Pro Ser
195                 200                 205

ACA TTA GAG ACA TTT CTG GGA AGA CTT CCC ATG GTG TTT AAT GTG    0674
Thr Leu Glu Thr Phe Leu Gly Arg Leu Pro Met Val Phe Asn Val
210                 215                 220

GTC ATT TTG TCT GTA CAT GGA TAT TTT GGA CAG GCA CAT GTG CTC    0719
Val Ile Leu Ser Val His Gly Tyr Phe Gly Gln Ala His Val Leu
225                 230                 235

GGC TTG CCT GAC ACT GGT GGG CAG ATA GTT TAT ATA CTT GAC CAA    0764
Gly Leu Pro Asp Thr Gly Gly Gln Ile Val Tyr Ile Leu Asp Gln
240                 245                 250

GTG CGG TCT CTG GAA CAT GAA ATG CTC CAA CGA ATA AAG AAG CAA    0809
Val Arg Ser Leu Glu His Glu Met Leu Gln Arg Ile Lys Lys Gln
255                 260                 265

GGA CTA GAT GTG ACT CCT AGA ATT CTT ATC GTG AGT CGG TTG ATT    0854
Gly Leu Asp Val Thr Pro Arg Ile Leu Ile Val Ser Arg Leu Ile
270                 275                 280

CCT GAC GCT AAA GGG ACC ACG TGC AAT CAA CGT ATG GAG AAA GTC    0899
Pro Asp Ala Lys Gly Thr Thr Cys Asn Gln Arg Met Glu Lys Val
285                 290                 295

AGT GGA ACA GAG CAT GCT AGT ATC CTG AGA GTT CCT TTC CGA TCA    0944
Ser Gly Thr Glu His Ala Ser Ile Leu Arg Val Pro Phe Arg Ser
300                 305                 310

GAG AAA GGA ATC CTC CGC AAA TGG ATA TCT AGA TTT GAT GTA TGG    0989
```

|     |     |     |     |     |     |     |     |     |     |     |     |     |     |     |
|---|---|---|---|---|---|---|---|---|---|---|---|---|---|---|
| Glu 315 | Lys | Gly | Ile | Leu | Arg 320 | Lys | Trp | Ile | Ser | Arg 325 | Phe | Asp | Val | Trp |

| CCT | TAT | TTA | GAG | ACC | TTC | ACT | GAG | GAT | GCA | GCT | GGT | GAA | ATT | ATT | 1034 |
|---|---|---|---|---|---|---|---|---|---|---|---|---|---|---|---|
| Pro 330 | Tyr | Leu | Glu | Thr | Phe 335 | Thr | Glu | Asp | Ala | Ala 340 | Gly | Glu | Ile | Ile | |
| GGC | GAG | TTG | CAG | GGT | CGT | CCA | GAT | CTG | ATA | ATT | GGC | AAC | TAC | AGC | 1079 |
| Gly 345 | Glu | Leu | Gln | Gly | Arg 350 | Pro | Asp | Leu | Ile | Ile 355 | Gly | Asn | Tyr | Ser | |
| GAT | GGG | AAT | ATA | GTT | GCT | TCT | TTA | TTG | TCC | CAC | AAA | ATG | GGT | GTC | 1124 |
| Asp 360 | Gly | Asn | Ile | Val | Ala 365 | Ser | Leu | Leu | Ser | His 370 | Lys | Met | Gly | Val | |
| ACC | CAG | TGC | AAT | ATA | GCC | CAT | GCA | TTG | GAG | AAA | ACC | AAG | TAT | CCA | 1169 |
| Thr 375 | Gln | Cys | Asn | Ile | Ala 380 | His | Ala | Leu | Glu | Lys 385 | Thr | Lys | Tyr | Pro | |
| GAT | TCT | GAT | ATT | TAC | TGG | AAA | AGA | TTT | GAG | GAC | AAA | TAT | CAC | TTC | 1214 |
| Asp 390 | Ser | Asp | Ile | Tyr | Trp 395 | Lys | Arg | Phe | Glu | Asp 400 | Lys | Tyr | His | Phe | |
| TCG | TGT | CAA | TTT | TCA | GCT | GAC | TTG | ATG | GCA | ATG | AAT | CAT | GCT | GAT | 1259 |
| Ser 405 | Cys | Gln | Phe | Ser | Ala 410 | Asp | Leu | Met | Ala | Met 415 | Asn | His | Ala | Asp | |
| TTC | ATC | ATT | ACG | AGT | ACT | TAC | CAA | GAG | ATA | GCT | GGA | ACG | AAG | AAT | 1304 |
| Phe 420 | Ile | Ile | Thr | Ser | Thr 425 | Tyr | Gln | Glu | Ile | Ala 430 | Gly | Thr | Lys | Asn | |
| ACT | GTT | GGT | CAA | TAT | GAA | AGC | CAT | AAG | GCC | TTT | ACT | TTT | CCG | GGG | 1349 |
| Thr 435 | Val | Gly | Gln | Tyr | Glu 440 | Ser | His | Lys | Ala | Phe 445 | Thr | Phe | Pro | Gly | |
| CTG | TAT | CGG | GTG | GTT | CAC | GGG | ATT | GAT | GTC | TTT | GAT | CCC | AAG | TTT | 1394 |
| Leu 450 | Tyr | Arg | Val | Val | His 455 | Gly | Ile | Asp | Val | Phe 460 | Asp | Pro | Lys | Phe | |
| AAT | ATT | GTC | TCG | CCA | GGG | GCA | GAC | ATG | GCC | ATC | TAC | TTC | CCA | TTT | 1439 |
| Asn 465 | Ile | Val | Ser | Pro | Gly 470 | Ala | Asp | Met | Ala | Ile 475 | Tyr | Phe | Pro | Phe | |
| TCA | GAG | AAG | GAT | GTC | ACC | TGT | CTC | ACT | TCA | CTT | CAT | AGA | CTT | ATA | 1484 |
| Ser 480 | Glu | Lys | Asp | Val | Thr 485 | Cys | Leu | Thr | Ser | Leu 490 | His | Arg | Leu | Ile | |
| GAG | CAG | CTC | CTA | TTC | AAA | CCT | GAG | CAG | AAC | GAA | GAA | CAC | ATT | GGT | 1529 |
| Glu 495 | Gln | Leu | Leu | Phe | Lys 500 | Pro | Glu | Gln | Asn | Glu 505 | Glu | His | Ile | Gly | |
| GTA | TTA | GAT | GAT | ACC | TCA | AAG | CCA | ATT | ATA | TTT | TCC | ATG | GCG | AGG | 1574 |
| Val 510 | Leu | Asp | Asp | Thr | Ser 515 | Lys | Pro | Ile | Ile | Phe 520 | Ser | Met | Ala | Arg | |
| CTA | GAC | CGT | GTG | AAG | AAT | ATA | ACA | GGG | CTG | GTA | GAG | TGC | TAT | GGC | 1619 |
| Leu 525 | Asp | Arg | Val | Lys | Asn 530 | Ile | Thr | Gly | Leu | Val 535 | Glu | Cys | Tyr | Gly | |
| AAG | AAT | GCG | AAA | CTC | AGG | GAA | CTG | GCA | AAC | CTG | GTT | GTA | GTG | GCT | 1664 |
| Lys 540 | Asn | Ala | Lys | Leu | Arg 545 | Glu | Leu | Ala | Asn | Leu 550 | Val | Val | Val | Ala | |
| GGG | TAC | AAT | GAT | GTA | AAA | AAG | TCG | AAT | GAC | AGG | GAG | GAA | ATT | GCC | 1709 |
| Gly 555 | Tyr | Asn | Asp | Val | Lys 560 | Lys | Ser | Asn | Asp | Arg 565 | Glu | Glu | Ile | Ala | |
| GAA | ATC | GAG | AAG | ATG | CAC | AGG | CTT | ATA | CAG | GAG | TAT | AAT | TTA | AGA | 1754 |

```
             Glu  Ile  Glu  Lys  Met  His  Arg  Leu  Ile  Gln  Glu  Tyr  Asn  Leu  Arg
             570            575                      580

GGA CAA TTT CGC TGG ATT GCT TCT CAA ACA AAT AGA GTA CGA AAT              1799
Gly Gln Phe Arg Trp Ile Ala Ser Gln Thr Asn Arg Val Arg Asn
585                     590                     595

GGT GAA CTC TAT CGC TAC ATT TGT GAC AAA GGA GGT ATT TTT GCG              1844
Gly Glu Leu Tyr Arg Tyr Ile Cys Asp Lys Glu Gly Ile Phe Ala
600                     605                     610

CAG CCT GCA TTT TAT GAA GCA TTT GGG CTT ACA GTT GTT GAA GCC              1889
Gln Pro Ala Phe Tyr Glu Ala Phe Gly Leu Thr Val Val Glu Ala
615                     620                     625

ATG ACC TGT GGT CTT CCC ACA TTT GCT ACC TGC CAC GGT GGT CCA              1934
Met Thr Cys Gly Leu Pro Thr Phe Ala Thr Cys His Gly Gly Pro
630                     635                     640

GCT GAG ATT ATA GAA GAC GGT GTT TCA GGA TTT CAT ATC GAT CCA              1979
Ala Glu Ile Ile Glu Asp Gly Val Ser Gly Phe His Ile Asp Pro
645                     650                     655

TAT CAT GCT GAT CAG GCA GAA AAA ATG ACT GAA TTC TTT GTC AAG              2024
Tyr His Ala Asp Gln Ala Glu Lys Met Thr Glu Phe Phe Val Lys
660                     665                     670

TGC AGA GAG GAT CCA AAC TAC TGG ACT AAA ATC TCT GCA GGA GGG              2069
Cys Arg Glu Asp Pro Asn Tyr Trp Thr Lys Ile Ser Ala Gly Gly
675                     680                     685

TTA CTA AGG ATC AAA GAA AGA TAT ACC TGG CAA AAG TAT TCT GAA              2114
Leu Leu Arg Ile Lys Glu Arg Tyr Thr Trp Gln Lys Tyr Ser Glu
690                     695                     700

AGG TTA ATG ACA TTG GCA GGG GTG TAT GGT TTC TGG AAA TAT GTC              2159
Arg Leu Met Thr Leu Ala Gly Val Tyr Gly Phe Trp Lys Tyr Val
705                     710                     715

TCT AAA CTA GAG AGA AGA GAG ACA CGA CGT TAT CTT GAG ATG TTC              2204
Ser Lys Leu Glu Arg Arg Glu Thr Arg Arg Tyr Leu Glu Met Phe
720                     725                     730

TAC ATT TTG AAG TTC CGT GAT CTG GCC AAC TCT GTT CCG CTG GCA              2249
Tyr Ile Leu Lys Phe Arg Asp Leu Ala Asn Ser Val Pro Leu Ala
735                     740                     745

ACA GAT GAA GAG CCT TCT ACT ACT GAT GCA GTT GCG ACA TTC CGT              2294
Thr Asp Glu Glu Pro Ser Thr Thr Asp Ala Val Ala Thr Phe Arg
750                     755                     760

GGA CCT TGA ACGCTGCTGC TTACTGAGGT TCCAAGTTGT GTATATATTA                  2343
Gly Pro End

CTGTGAAAGG AATAAGTGTA GCTACACAAA AGGTTCTCAA CTATTAGTAT                   2393

CTTCTCTGTG TAAATAACGA GAGTGAAAAA TGTAATATTG TTGATGTCTT                   2443

GAAAACTGAG TTTGCTTTGT TTATTTTTAA GTGTATGACA ATATGTATCA                   2493

TATAACGGAT TCTTCAGTGA TCATATCAAA AACTACTGAC CATCGAAGTT                   2543

AATGAAAATC GACAGCAACA                                                    2563
```

These sequences can also be combined together in a suitable plasmid which leads to a combination of the individual characteristics, conditioned by the expression of the protein.

The promoter should ensure that the foreign gene is expressed in the plant. The promoter can be so chosen that the expression occurs only in specified tissues, at a determined time point in the plant's development or at a time point determined by outside influences. The promoter can be homologous or heterologous to the plant. Suitable promoters are e.g. the promoter of the 35S RNA of the cauliflower mosaic virus, the patatin promoter B33 (Rocha-Sosa et al. (1989) EMBO J 8: 23–29) or a promoter that ensures an expression only in photosynthetically active tissues. Other promoters can be used which ensure expression only in specified organs, such as the root, tuber, seed, stem or specified cell types such as mesophyllic, epidermal or transport cells.

The coding sequences described herein contain the information for the formation of an mRNA for the large subunit of the ADP-glucose-pyrophosphorylase and the sucrose-phosphate-synthase (SPS) and a part of the information for formation of the small subunit of the ADP-glucose-pyrophosphorylase as well as the sucrose-synthase, that are suitable for the formation of anti-sense RNA to the corresponding genes. Whether a translatable mRNA or an anti-sense nucleic acid is formed, depends on the orientation of the coding sequence in relation to the promoter. If the 3' end of the coding sequence is fused to the 3' end of the promoter, an anti-sense RNA results, while fusion of the 5' end of the coding to the 3' end of the promoter produces a translatable RNA. The latter leads to an increase of the enzyme activity in the cell, while the former leads to a reduction of the enzyme activity in the cell.

The coding sequence for the large and small subunit of the ADP-glucose-pyrophosphorylase, the sucrose phosphate synthase and the sucrose synthase can be one of those described in this invention or can be one that is derived by modifications of the sequences described above. Thereby especially modifications of the sequences can be considered which lead to by-passing of the plant's own regulation mechanisms. Modifications to the DNA sequences of the invention can be by known methods, such as e.g. base exchange or targeted or non-targeted mutagenesis. The so-formed derivatives of the DNA sequences of the invention are also within the scope of the invention.

With plasmids, which contain one or more of the DNA sequences of the invention, sugar beet can be transformed with the object of raising and/or reducing the enzyme activity and/or the change of the sucrose concentration.

For the introduction of the DNA sequences of the invention in sugar beet, a large number of cloning vectors are available, which contain a replication signal for *E. coli* and a marker, which allows a selection of the transformed cells. According to the introduction method of the desired gene in the plant, other DNA sequences may be suitable. Should the Ti- or Ri-plasnid be used, e.g. for the transformation of the plant cell, then at least the right boundary, often however, both the right and left boundary of the Ti- and Ri-Plasmid T-DNA, is attached, as a flanking region, to the gene being introduced. The use of T-DNA for the transformation of plants cells has been intensively researched and is well described in EP 120 516; Hoekama, In: The Binary Plant Vector System, Offset-drukkerij Kanters B. V. Alblasserdam, (1985), Chapter V; Fraley, et al., Crit. Rev. Plant Sci., 4:1–46 and An et al. (1985) EMBO J. 4: 277–287. Once the introduced DNA is integrated in the genome, it is generally stable there and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells, which lack the introduced DNA.

For the introduction of DNA into a plant, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium, which contains antibiotics or biocides for the selection. The resulting plants can then be tested for the presence of introduced DNA. No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al.(1986) Plant Cell Reports 5: 81–84). These plants can be grown normally and crossed with plants, that possess the same transformed genes or different genes. The resulting hybrid individuals have the corresponding phenotypical properties.

In order to understand the examples forming the basis of this invention all the processes necessary for these tests and which are known per se will first of all be listed:

1. Cloning process

The vectors pUC 18/19 and M13mp10 series (Yanisch-Perron et al. (1985) Gene 33: 103–119), as well as the vector EMBL 3 (Frischauf et al. (1983) J Mol Biol 170: 827–842) were used for cloning.

For the plant transformations, the gene constructs were cloned in the binary vector BIN 19 (Bevan (1984) Nucl. Acids Res 12: 8711–8720)

2. Bacterial strains

The *E. coli* strain BMH71-18 (Messing et al., Proc. Natl. Acad. Sci. USA (1977), 24, 6342–6346) or TB1 was used for the pUC and M13 mP vectors.

For the vector BIN19, the *E. coli* strain TB1 exclusively, was used. TB1 is a recombinant-negative, tetracycline-resistant derivative of strain JM101 (Yanisch-Perron et al., Gene (1985), 33, 103–119). The genotype of the TB1 strain is (Bart Barrel, personal communication): F' (traD36, proAB, lacI, lacZΔM15), Δ(lac, pro), SupE, this, recA, Sr1::Tn10(TcR).

The transformation of the plasmids into the potato plants was carried out using *Agrobacterium tumefaciens* strain LBA4404 (Bevan, (1934), Nucl. Acids Res. 12, 8711–8720). TransporTation of *Agrobacterium tumefaciens*

In the case of BIN19 derivatives, the insertion of the DNA into the Agrobacterium was effected by direct transformation in accordance with the method of Holsters et al., (1978) (Mol Gene Genet 163: 181–187). The plasmid DNA of the transformed Agrobacterium was isolated in accordance with the method of Birnboim and Doly (1979) (Nucl Acids Res 7: 1513–1523) and was analysed by gel electrophoresis after suitable restriction cleavage.

4. Sucrose phosphate-synthase activity test

The sucrose phosphate-synthase activity was determined according to the method of Siegel and Stitt (1990, Plant Science 66: 205–210) in a two stage analysis. To 180 $\mu$l of a solution of 50 mM HEPES/KOH (pH 7.4), 5 mM magnesium chloride, 5 mM fructose-6-phosphate, 25 mM glucose-6-phosphate and 6 mM uridine-5'-diphosphoglucose, 20 μl of probe was added and incubated for 10 minutes at 25° C. It was heated for 3 minutes at 95° C., to complete the reaction. After centrifuging, the supernatant was spectroscopically analysed for the liberation of uridine-5'-diphosphate, whereby a pyruvate-kinase coupling enzyme reaction was used. Preparations without hexose phosphate, as well as the measurement of the recovery of added uridine-5'-diphosphate act as controls.

EXAMPLES

Example 1

Cloning of cDNA to large and small subunits of the ADP glucose pyrophosphorylase of sugar beet.

From the storage roots of 3–4 month old sugar beet plants grown in the greenhouse, RNA was isolated according to the method of Logemann et al (1987, Anal Biochem 163, 16–20). Resulting from poly-A+-RNA, a cDNA library was laid down according to the method of Gubler and Hoffmann (1983, Gene 25, 263) in the expression vector Lambda Zap II XR. To this there was used an oligo-dT primer provided with an XhoI recognising position and for synthesis of the first cDNA strand, methylated cytidine nucleotide was inserted. After synthesis of the two strands, an EcoRI-adaptor was attached and removed to one side by again cutting with the restriction endonuclease XhoI. In this way the hemimethylation of cDNA was hindered so that an internal XhoI recognition position is cut. By these procedures there is obtained a population of cDNA molecules that can be cloned directly into the EcoRI/XhoI cut DNA of the phage Lambda. After packing of recombinant phage-DNA in phage heads, 200000 plaque forming units of the bank were plated out for infection of a bacterial colony and then each is probed with the total cDNA fragment of the large and/or subunit of the AGPase of potato (Müller-Roeber et al., 1990, MGG 224, 136–146) as an EcoRI-fragment. The recombinant phages corresponding to the hybridising signal were isolated. By in vivo excision, plasmids were cut out from the Lambda zap-genome, which carry a double stranded cDNA as insertion. The plasmids were transformed in bacterial cells. The plasmid-DNA was then propagated in the bacteria. After checking the size of the insertions, individual clones were analysed by determination of the primary sequence.

Example 2

Cloning of cDNA to sucrose-phosphate-synthase (SPS) from sugar beet.

From the storage roots of 3–4 month old sugar beet plant grown in the greenhouse, RNA was isolated according to the method of Logemann et al (1987, Anal Biochem 163, 16–20). Resulting from poly-A+-RNA, a cDNA library was laid down according to the method of Gubler and Hoffmann (1983, Gene 25, 263) in the expression vector Lambda Zap II XR. To this there was used an oligo-dT primer provided with an XhoI recognising position and for synthesis of the first cDNA strand, methylated cytidine nucleotide was inserted. After synthesis of the two strands, an EcoRI-adaptor was attached and removed to one side by again cutting with the restriction endonuclease XhoI. In this way the hemimethylation of cDNA was hindered so that an internal XhoI recognition position is cut. By these procedures there is obtained a population of cDNA molecules that can be cloned directly into the EcoRI/XhoI cut DNA of the phage Lambda. After packing of recombinant phage-DNA in phage heads, 200000 plaque forming units of the bank were plated out for infection of a bacterial colony and then each is probed with the total cDNA fragment of the sucrose-phosphate-synthase (SPS) from spinach (Sonnewald, 1992, Planta) as NotI. The recombinant phages corresponding to the hybridising signal were isolated. By in vivo excision, plasmids were cut out from the Lambda zap-genome, which carry a double stranded cDNA as insertion. The plasmids were transformed in bacterial cells. The plasmid-DNA was then propagated in the bacteria. After checking the size of the insertions, individual clones were analysed by determination of the primary sequence.

Example 3

Cloning of cDNA to sucrose-synthase from sugar beet.

From the storage roots of 3–4 month old sugar beet plants grown in the greenhouse, RNA was isolated according to the method of Logemann et al (1987, Anal Biochem 163, 16–20). Resulting from poly-A+-RNA, a cDNA library was laid down according to the method of Gubler and Hoffmann (1983, Gene 25, 263) in the expression vector Lambda Zap II XR. To this there was used an oligo-dT primer provided with an XhoI recognising position and for synthesis of the first cDNA strand, methylated cytidine nucleotide was inserted. After synthesis of the two strands, an EcoRI-adaptor was attached and removed to one side by again cutting with the restriction endonuclease XhoI. In this way the hemimethylation of cDNA was hindered so that an internal XhoI recognition position is cut. By these procedures there is obtained a population of cDNA molecules that can be cloned directly into the EcoRI/XhoI cut DNA of the phage Lambda. After packing of recombinant phage-DNA in phage heads, 200000 plaque forming units of the bank were plated out for infection of a bacterial colony and then each is probed with both EcoRI/BglII sub fragments sucrose synthase from maize (Worrell et al., 1991, Plant Cell 3, 1121–1130). The recombinant phages corresponding to the hybridising signal were isolated. By in vivo excision, plasmids were cut out from the Lambda zap-genome, which carry a double stranded cDNA as insertion. The plasmids were transformed in bacterial cells. The plasmid-DNA was then propagated in the bacteria. After checking the size of the insertions, individual clones were analysed by determination of the primary sequence.

Example 4

Determination of the nuclectide sequence of the ADP glucose pyrophosphorylase, the sucrose synthase and the sucrose phosohate synthase of sugar beet and derivation of the corresponding amino acid sequences The nucleotide sequences of the instructions obtained from Examples 1–3, were determined by standard methods by means of the dideoxy method (Sanger et al. (1977) Proc. Natl. Acad. Sci. USA, 74, 5463–5467). The nucleotide sequences and the amino acid sequences derived therefrom are given in the sequence protocols Seq. ID No. 1–4.

The sequences are shown earlier; the protocols are as follows:
SEO ID NO: 1
SEQUENCE TYPE: Nucleotide with corresponding protein
SEQUENCE LENGTH: 1924 base pairs
STRANDEDNESS: single
TOPOLOGY: linear
MOLECULE TYPE: cDNA
ORIGINAL SOURCE
ORGANISM: *Beta vulgaris*
IMMEDIATE EXPERIMENTAL SOURCE: cDNA library in Phage Lamda zap FEATURES: from 206 to 1770 coding region
PROPERTIES: ADP-glucose-pyrophosphorylase, large subunit
SEO ID NO: 3
SEQUENCE TYPE: Nucleotide with corresponding protein
SEQUENCE LENGTH: 1763 base pairs
STRANDEDNESS: single
TOPOLOGY: linear
MOLECULE TYPE: cDNA
ORIGINAL SOURCE
ORGANISM: Beta vulgaris
IMMEDIATE EXPERIMENTAL SOURCE: cDNA library in Phage Lamda zap
FEATURES: from 3 to 1469 coding region
PROPERTIES: ADP-glucose-pyrophosphorylase, small subunit
SEO ID NO: 5
SEQUENCE TYPE: Nucleotide with corresponding protein
SEQUENCE LENGTH: 3635 base pairs
STRANDEDNESS: single
TOPOLOGY: linear
MOLECULE TYPE: cDNA
ORIGINAL SOURCE
ORGANISM: Beta vulgaris
IMMIEDIATE EXPERIMENTAL SOURCE: cDNA library in Phage Lamda zap
FEATURES: from 31 to 3164 coding region
PROPERTIES: Sucrose-phosphate-synthase
SEO ID NO: 7
SEQUENCE TYPE: Nucleotide with corresponding protein
SEQUENCE LENGTH: 2563 base pairs
STRANDEDNESS: single
TOPOLOGY: linear
MOLECULE TYPE: cDNA
ORIGINAL SOURCE
ORGANISM: Beta vulgaris
IMMMEDIATE EXPERIMENTAL SOURCE: cDNA library in Phage Lamda zap
FEATURES: from 3 to 2300 coding region
PROPERTIES: Sucrose synthase

---

We claim:

1. An isolated DNA molecule comprising a DNA sequence, wherein the sequence comprises Seq. ID No. 1.

2. An isolated DNA molecule comprising a DNA sequence wherein the sequence comprises Seq. ID No. 3.

3. An isolated DNA molecule comprising a DNA sequence wherein the sequence comprises Seq. ID No. 5.

4. An isolated DNA molecule comprising a DNA sequence wherein the sequence comprises Seq. ID No. 7.

5. An isolated DNA molecule selected from the group consisting of: (i) SEQ ID NO. 1; (ii) SEQ ID NO. 3; (iii) SEQ ID No. 5; (iv) SEQ ID NO. 7; and (v) SEQ ID NO. 1, SEQ ID NO. 3, SEQ ID NO. 5, and SEQ ID NO. 7.

6. An isolated DNA molecule having a sequence selected from the group consisting of SEQ ID NO. 1, SEQ ID NO. 3, SEQ ID NO. 5, and SEQ ID NO. 7.

7. An isolated DNA molecule having a nucleotide sequence comprising SEQ ID NO. 1, SEQ ID NO. 3, SEQ ID NO. 5, and SEQ ID NO. 7.

8. A plasmid comprising at least one isolated DNA molecule as in any ot claims 1, 2, 3, 4, 5, 6, or 7.

9. A plasmid comprising:
a promoter sequence;
at least one coding sequence selected from the group consisting of SEQ ID NO. 1, SEQ ID NO. 3, SEQ ID NO. 5, and SEQ ID NO, 7, wherein said coding sequence, upon expression produces a protein; and
a termination sequence.

10. A plasmid comprising:
a promoter sequence;
at least one coding sequence selected from the group consisting of SEQ ID NO. 1, SEQ ID NO. 3, SEQ ID NO. 5, and SEQ ID NO. 7, wherein said coding sequence is in an anti-sense orientation with respect to the promoter; and
a termination sequence.

11. A method for producing a transformed plant cell comprising transforming the plant cell so that it comprises and expresses an isolated DNA molecule as claimed in any one of claims 1, 2, 3, 4, 5, 6, or 7.

12. A method for producing a transformed plant comprising transforming a plant cell so that it comprises and expresses an isolated DNA molecule as claimed in any one of claims 1, 2, 3, 4, 5, 6, or 7 and regenerating the transformed plant from the plant cell.

13. A method for producing a transformed plant cell comprising transforming the plant cell so that it comprises an isolated DNA molecule as claimed in any one of claims 1, 2, 3, 4, 5, 6, or 7 in an anti-sense orientation.

14. A method for producing a transformed plant comprising transforming a plant cell so that it comprises an isolated DNA molecule as claimed in any one of claims 1, 2, 3, 4, 5, 6, or 7 in an anti-sense orientation and regenerating the transformed plant from the plant cell.

15. A method for producing a transformed plant cell comprising transforming the plant cell so that it comprises the plasmid of claim 8 and expresses the isolated DNA molecule therein.

16. A method for producing a transformed plant comprising transforming a plant cell so that it comprises the plasmid of claim 8 and expresses the isolated DNA molecule therein, and regenerating the transformed plant from the plant cell.

17. A method for producing a transformed plant cell comprising transforming the plant cell so that it comprises the plasmid of claim 8 and the isolated DNA molecule therein is in an anti-sense orientation.

18. A method for producing a transformed plant comprising transforming a plant cell so that it comprises the plasmid of claim 8 and the isolated DNA molecule therein is in an anti-sense orientation, and regenerating the transformed plant from the plant cell.

19. A method of producing a plant or plant cell comprising the steps of:

producing a DNA molecule comprising the following sequences:
  (i) a promoter which is active in said plant or plant cell,
  (ii) a structural DNA sequence selected from the group consisting of SEQ ID NO. 1, SEQ ID NO. 3, SEQ ID NO. 5, and SEQ ID NO. 7 positioned in a sense orientation; and
transferring and incorporating said DNA molecule into the genome of a plant cell.

20. A method of producing a plant or plant cell comprising the steps of:
producing a DNA molecule comprising the following sequences:
  (i) a promoter which is active in said plant or plant cell,
  (ii) a structural DNA sequence selected from the group consisting of SEQ ID NO. 1, SEQ ID NO. 3, SEQ ID NO. 5, and SEQ ID NO. 7 positioned in an anti-sense orientation; and
transferring and incorporating said DNA molecule into the genome of a plant cell.

21. A transformed plant cell comprising at least one isolated DNA molecule as in any of claims 1, 2, 3, 4, 5, 6, or 7.

22. A transformed plant comprising at least one isolated DNA molecule as in any of claims 1, 2, 3, 4, 5, 6, or 7.

23. A transgenic sugar beet plant comprising at least one isolated DNA molecule as in any of claims 1, 2, 3, 4, 5, 6, or 7.

24. A plant or plant cell transformed with a plasmid according to claim 9.

25. A plant or plant cell transformed with a plasmid according to claim 10.

26. A transformed plant cell comprising the plasmid of claim 8.

27. A transformed plant comprising the plant cell of claim 21.

28. A transformed plant comprising the plant cell of claim 26.

29. A transformed plant comprising the plasmid of claim 8.

30. A transformed plant comprising an isolated DNA molecule having a nucleotide sequence comprising SEQ ID. NO. 1.

31. A transformed plant comprising an isolated DNA molecule having a nucleotide sequence comprising SEQ ID. NO. 3.

32. A transformed plant comprising an isolated DNA molecule having a nucleotide sequence comprising SEQ ID. NO. 5.

33. A transformed plant comprising an isolated DNA molecule having a nucleotide sequence comprising SEQ ID. NO. 7.

34. A transformed plant comprising an isolated DNA molecule having a nucleotide sequence comprising SEQ ID. NO. 1, SEQ ID NO. 3, SEQ ID NO. 5, and SEO ID NO. 7.

35. A transformed plant cell comprising an isolated DNA molecule therein, and regenerating the plant from the plant cell having a nucleotide sequence selected from the group consisting of: SEQ ID. NO. 1; SEQ ID NO. 3; SEQ ID NO. 5; SEQ ID NO. 7; and SEQ ID. NO. 1, SEQ ID NO. 3, SEQ ID NO. 5, and SEQ ID NO. 7.

* * * * *